US011521726B2

(12) United States Patent
Giles et al.

(10) Patent No.: US 11,521,726 B2
(45) Date of Patent: Dec. 6, 2022

(54) SYSTEM AND METHOD FOR MONITORING DRUG DELIVERY

(71) Applicant: Sonara Health, Inc., Dallas, TX (US)

(72) Inventors: Michael Giles, Dallas, TX (US); John Thomas Menchaca, San Antonio, TX (US); Avinash Prasanna Jayaraman, Chicago, IL (US); Dimitri Macris, Dallas, TX (US)

(73) Assignee: Sonara Health, Inc., Dallas, TX (US)

( * ) Notice: Subject to any disclaimer, the term of this patent is extended or adjusted under 35 U.S.C. 154(b) by 0 days.

(21) Appl. No.: 17/540,717

(22) Filed: Dec. 2, 2021

(65) Prior Publication Data
US 2022/0238199 A1 Jul. 28, 2022

Related U.S. Application Data

(60) Provisional application No. 63/142,831, filed on Jan. 28, 2021.

(51) Int. Cl.
*G16H 20/10* (2018.01)
*G06K 7/14* (2006.01)
(Continued)

(52) U.S. Cl.
CPC .......... *G16H 20/10* (2018.01); *G06K 7/1417* (2013.01); *G06V 40/20* (2022.01); *G16H 40/67* (2018.01)

(58) Field of Classification Search
CPC ........ G16H 20/10; G16H 40/67; G06V 40/20; G06K 7/1417
(Continued)

(56) References Cited

U.S. PATENT DOCUMENTS

2014/0257852 A1* 9/2014 Walker ................... G06Q 10/10
705/3
2016/0147976 A1* 5/2016 Jain ........................ G16H 20/10
705/2
(Continued)

OTHER PUBLICATIONS

Subbaraman et. Al., Digital adherence technologies for the management of tuberculosis therapy: mapping the landscape and research priorities, Oct. 11, 2018, BMJ Global Health, vol. 3, Issue 5, http://dx.doi.org/10.1136/bmjgh-2018-001018 (Year: 2018).*
(Continued)

*Primary Examiner* — Joy Chng
(74) *Attorney, Agent, or Firm* — Whitmyer IP Group LLC

(57) ABSTRACT

A system for monitoring drug delivery including a container having a medicine, the medicine associated with a patient and a code on an outside of the container. The system also including a user device having a camera and software executing on a computer readable medium for initiating recording of a video with the camera, prompting the patient to show the code in the video and show the taking of the medicine in the video. The system further includes a computer receiving the video, the computer having a datastore with a plurality of profiles, one of the plurality of profiles being a patient profile associated with the patient and software executing on a computer readable medium for storing the video, verifying the association of the medicine and the patient, identifying movement in the video, and generating a score indicative of the likelihood the medicine was taken by the patient.

18 Claims, 18 Drawing Sheets

(51) Int. Cl.
*G06V 40/20* (2022.01)
*G16H 40/67* (2018.01)

(58) Field of Classification Search
USPC .......................................................... 705/2–3
See application file for complete search history.

(56) References Cited

U.S. PATENT DOCUMENTS

2019/0087951 A1* 3/2019 Hanina ................. G16H 50/20
2021/0065863 A1* 3/2021 Hopen .................. G16H 80/00

OTHER PUBLICATIONS

Pérez-Jover et al., Mobile Apps for Increasing Treatment Adherence: Systematic Review, Aug. 16, 2019, Journal of Medical Internet Research, vol. 21, No. 6, doi: 10.2196/12505, https://www.jmir.org/2019/6/e12505 (Year: 2019).*
PCT International Search Report & Written Opinion of the International Searching Authority; Application No. PCT/US2022/070291; Completed: Mar. 31, 2022; dated Mar. 31, 2022; 13 Pages.

* cited by examiner

SYSTEM AND METHOD FOR MONITORING DRUG DELIVERY

CROSS-REFERENCE TO RELATED APPLICATIONS

This patent application claims the benefit, under 35 U.S.C. § 119(e), of U.S. Provisional Application Ser. No. 63/142,831, filed on Jan. 28, 2021 the contents of which are incorporated herein by reference in its entirety.

TECHNICAL FIELD

The disclosure herein generally relates to systems and methods for monitoring drug delivery. More specifically, the disclosure relates to patient led adherence to drug consumption by monitoring and tracking prescription medication dosage and consumption. The system may use a unique combination of technologies including artificial intelligence-based safety monitoring, facial recognition, tamper-aware "smart" packaging or tamper-evident barcode, e.g., QR codes or RFID labels, medication packaging, and a bespoke smart device/phone website/application designed to track and report medication usage data in real-time to a physician or caregiver.

BACKGROUND

Opioids are used for a variety of purposes such as treating pain, mental disorders, and physical disorders, among others. Opioids are powerful and in many cases addictive. As such, regulating adherence to opioid regimes is important not only to patients but their families and medical workers.

Opioid use disorder ("OUD") and addiction remain prevalent in the U.S. and worldwide. Over three (3) million Americans and sixteen (16) million individuals worldwide have had or currently suffer from OUD. Roughly 21-29% of patients prescribed opioids for chronic pain misuse them, and between 8-12% develop an OUD. The use of opioids to treat OUD is subject to federal regulations beyond those that apply to the same medications used for other purposes (e.g., treating pain).

Federally certified opioid treatment programs ("OTPs")—often called methadone clinics—offer these medications alongside counseling and other services for OUD patients. With few exceptions, the use of methadone to treat opioid addiction is limited to OTPs certified by the Substance Abuse and Mental Health Services Administration ("SAMHSA"). A patchwork of state and local regulations often mandates further regulatory burdens, which limit the number and distribution of OTP locations.

OUD and opioid addiction affect individuals from all socioeconomic and educational backgrounds. The consequences are devastating, including the rising incidence of neonatal abstinence syndrome due to opioid misuse during pregnancy, and the spread of infectious diseases such as HIV and hepatitis C due to the increase in injection drug use.

The treatment for OUD can be a sensitive topic which individuals may wish to keep private. Accordingly, anonymity and autotomy are highly valued by both patients and care providers. A telehealth medication monitoring system satisfies the need for anonymity and autotomy however such known systems suffer from a lack of security, versatility to use different forms of medication, incentives for adherence to dosage regimes, and workflow automation for clinicians. Known systems fail to find a balance between patient privacy and autonomy against regulation and monitoring medication dosage, especially highly regulated and addictive substances, while also providing clinical workflow automation and clinic incentives. Furthermore, telehealth systems have the added difficulty of compliance with Health Insurance Portability and Accountability Act ("HIPAA") where sensitive information is being transferred to/stored in remote locations.

Medication-assisted treatment ("MAT") with methadone, buprenorphine, or naltrexone is central to the treatment of OUD. Although all three medications are effective, they are not equivalent or interchangeable. Methadone is a proven and effective opioid medication used to treat OUD, shown to extend retention in treatment programs, reduce overdose death rates and further illicit drug use. Methadone is a full opioid agonist that binds to and activates opioid receptors in the brain. It suppresses withdrawal symptoms in detoxification treatment and controls the craving for opioids in maintenance treatment. Naltrexone requires detoxification prior to initiation, which can be challenging and painful. The risk of relapse during this process is substantial and is a significant barrier to antagonist medications. Buprenorphine, a partial opioid agonist, is less addictive than methadone but less effective in detoxification and maintenance treatment, and utilization remains low (around 20% of OUD sufferers). Accordingly, strict adherence to medication dosage regimes is highly important.

According to SAMHSA, the greatest barriers that keep individuals with OUD from receiving treatment are as follows: 1) accessibility, to be compliant with federal laws concerning methadone overdose and diversion risk, OUD patients must visit a specialized clinic daily for directly observed dosing. This prevents many patients from receiving methadone due to a variety of reasons including geography, personal and work obligations, travel, and access to transportation; 2) acceptability, all non-methadone medications require some form of highly uncomfortable opioid detox prior to treatment initiation. Many OUD sufferers are unwilling to undergo detox and instead continue to use opioids illicitly; 3) availability, opioid treatment programs do not exist in 39% of counties nationally. Individuals living in rural areas report higher rates of prescription opioid misuse than urban residents, yet only about 3% of all opioid treatment programs are located in rural areas; 4) privacy, individuals, especially those living in rural locations, commonly cite privacy as a barrier to starting OUD treatment. Concerns include being the subject of gossip or marginalization.

Medication monitoring systems known in the art include the etectRx ID-Cap, the SMRxT NOMI vial system, AiCure, Welldoc, Medisafe, DynamiCare Health, Kaden, Ophelia, Boulder, Workit, and Emocha.

The etectRx ID-Cap system uses a consumable microchip to monitor drug delivery. This system notably requires the ingestion of a microchip. Patients have expressed that ingesting a microchip is overly invasive. The use of a microchip adds substantial cost.

The SMRxT NOMI vial system tracks contents removed or added to a smart vial. This system notably lacks the ability to verify what is added to the vial, or that whatever is removed from the vial is consumed.

The AiCure applies machine learned algorithms to video data to track adherence to pill-based regimes. By recording a patient's facial expressivity, verbal acoustics, speech characteristics, and patterns of movement in conjunction with visually confirming the taking of medication, AiCure attempts to report clinical trial results remotely. This system notably does not employ tamper-evident packaging, or tamper-evident bar code or near field communication (NFC) labels.

Welldoc system uses tablet-based adherence tracking and is unable to track liquid medication. The Welldoc system also uses generic workflow management which limits efficiency. The Medisafe system suffers from similar problems.

DynamiCare Health is a contingency management system that does not implement medication tracking and dosage regime adherence.

The Kaden system is unable to track liquid medication while the Emocha system has insecure medication tracking, and no workflow automation for clinicians.

The Ophelia, Boulder, and Workit systems are not suitable for use with all types of medication, including specifically methadone, and these systems lack workflow automation for clinicians.

Furthermore, known systems work only with pill-based medication. The present invention works with any type of medication, including pill-based, liquid-based, and aerosol medication.

Other deficiencies of known systems include a lack of patient engagement to adhere to dosage regimes, providing support though addiction and OUD treatment.

SUMMARY

When asked: "instead of going to the clinic daily, would you be willing to send your doctor brief daily videos of yourself taking methadone?", 88% of survey participants responded "yes". For these and other reasons known to a person of an ordinary skill in the art, what is needed is a secure telehealth system for monitoring drug delivery.

The present teachings are designed to address the aforementioned hurdles while mitigating safety and diversion risks beyond what is possible with currently available technologies. By offering an OTP-specific telemedicine solution that supports methadone, the present invention has the potential to significantly expand access to this life-saving therapy.

A goal of the present teachings is to provide a unique telehealth platform that aligns incentives and brings value to each of the "three P's" of healthcare: patients, providers, and payors.

For patients, the present teachings address the four main barriers to treatment: accessibility, acceptability, availability, and privacy. Patients commonly cite privacy as a barrier to treatment—especially those living in rural locations. For example, patients often need to publicly line up outside a clinic daily for hours. Access to treatment via telehealth will not only protect privacy but also reduce travel time, saving patients on average 13 hours per month.

For providers, the present teachings may 1) enhance clinical decision-making by providing previously unknown medication handling and adherence data, 2) save time (e.g., AI-enhanced workflow allows batch processing of multiple dosing sessions at once), and 3) lead to improved treatment initiation and retention rates, therefore increasing providers' revenue over time (e.g., up to 40% more revenue per patient/month compared to in-person workflows).

For payors, the enhanced access to quality care provided by the presently disclosed system may lead to reduced healthcare resource utilization by OUD patients (for instance, less visits to the ER).

Another goal of the present teachings is to provide a system to track medication dosing adherence remotely and reliably and provide patient autotomy. Patients cite the burden associated with daily visits, such as long drives and the cost of gas. The present invention seeks to provide a solution that will not only address common barriers to receiving treatment, but also alleviate the stigma and inconvenience associated with treatments for opioid addiction.

Another goal of the present teachings is to streamline generic workflow through remote assessments and automatic billing increasing clinic revenue. Through the present invention providers may receive the data needed to identify the medical indication required for billing new telemedicine billing codes for Medicare patients (e.g., missed dose, exemption take-home doses) or remote evaluation codes for Medicaid patients.

Another goal of the present teachings is to create patient accountability and provider trust needed for take-home dosage regimes, especially those for at risk patients and for potentially dangerous medications.

Another goal of the present teachings is to monitor and guide patient consumption of dangerous, heavily regulated, expensive, or epidemiologically consequential medication regimes. For example, methadone for opioid addiction, opioid-based therapy for chronic pain, and antibiotic therapy for tuberculosis.

Another goal of the present teachings is to provide secure medication dosing though the use of multifactor authentication and/or tamper-evident codes. In addition to providing secure medication dosing the present invention also seeks to provide HIPAA compliant privacy and security measures.

Another goal of the present teachings is to provide real time feedback on patient adherence to medication regimes to caregivers, guardians, prescribers, payors, or other stakeholders.

Another goal of the present teachings is to provide medication adherence or non-adherence behaviors for contextually guided interventions.

In one embodiment the system for monitoring drug delivery may include a container having a medicine disposed inside, the medicine associated with a patient and a machine-readable code on an outside of the container. The system may also include a user device having a camera and software executing on a computer readable medium for initiating recording of a video with the camera, prompting the patient to show the machine-readable code in the video, and prompting the patient to show the taking of the medicine in the video. The system may further include a computer receiving the video, the computer having a datastore with a plurality of profiles, one of the plurality of profiles being a patient profile associated with the patient and software executing on a computer readable medium for storing the video and associating the video with the patient profile, verifying the association of the medicine and the patient using the code, identifying movement of the patient in the video, and generating a score based on the verifying and the identifying, the score indicative of the likelihood the medicine was taken by the patient.

In another embodiment the system for monitoring drug delivery may include a container having a medicine disposed inside, the medicine associated with a patient and a machine-readable code on an outside of the container. The system may also include a user device having a camera and software executing on a computer readable medium for initiating recording of a video with the camera, prompting the patient to show the machine-readable code in the video, and prompting the patient to show the taking of the medicine in the video. The system may further include a computer receiving the video, the computer having a datastore with a plurality of profiles, one of the plurality of profiles being a patient profile associated with the patient. The system may have software executing on a computer readable medium for storing the video and associating the video with the patient profile, verifying the association of the medicine and the patient using the code, identifying movement of the patient in the video, and generating a score based on the verifying and the identifying. The score being indicative of the likelihood the medicine was taken by the patient. The system may additionally include a provider device having software executing on a computer readable medium for, receiving and displaying the score and the video, receiving a user input adjusting the score; and transmitting the user input to the datastore.

BRIEF DESCRIPTION OF THE DRAWINGS

FIGS. 5A-B are diagrams depicting one embodiment of the provider review interface of a system for monitoring drug delivery.

FIGS. 6A-F are diagrams depicting one embodiment of the provider management interface of a system for monitoring drug delivery.

DETAILED DESCRIPTION

The present teachings are described more fully hereinafter with reference to the accompanying drawings, in which the present embodiments are shown. The following description illustrates the present teachings by way of example, not by way of limitation of the principles of the present teachings.

The present teachings have been described in language more or less specific as to structural features. It is to be understood, however, that the present teachings are not limited to the specific features shown and described, since the product herein disclosed comprises preferred forms of putting the present teachings in effect.

Figure 1:
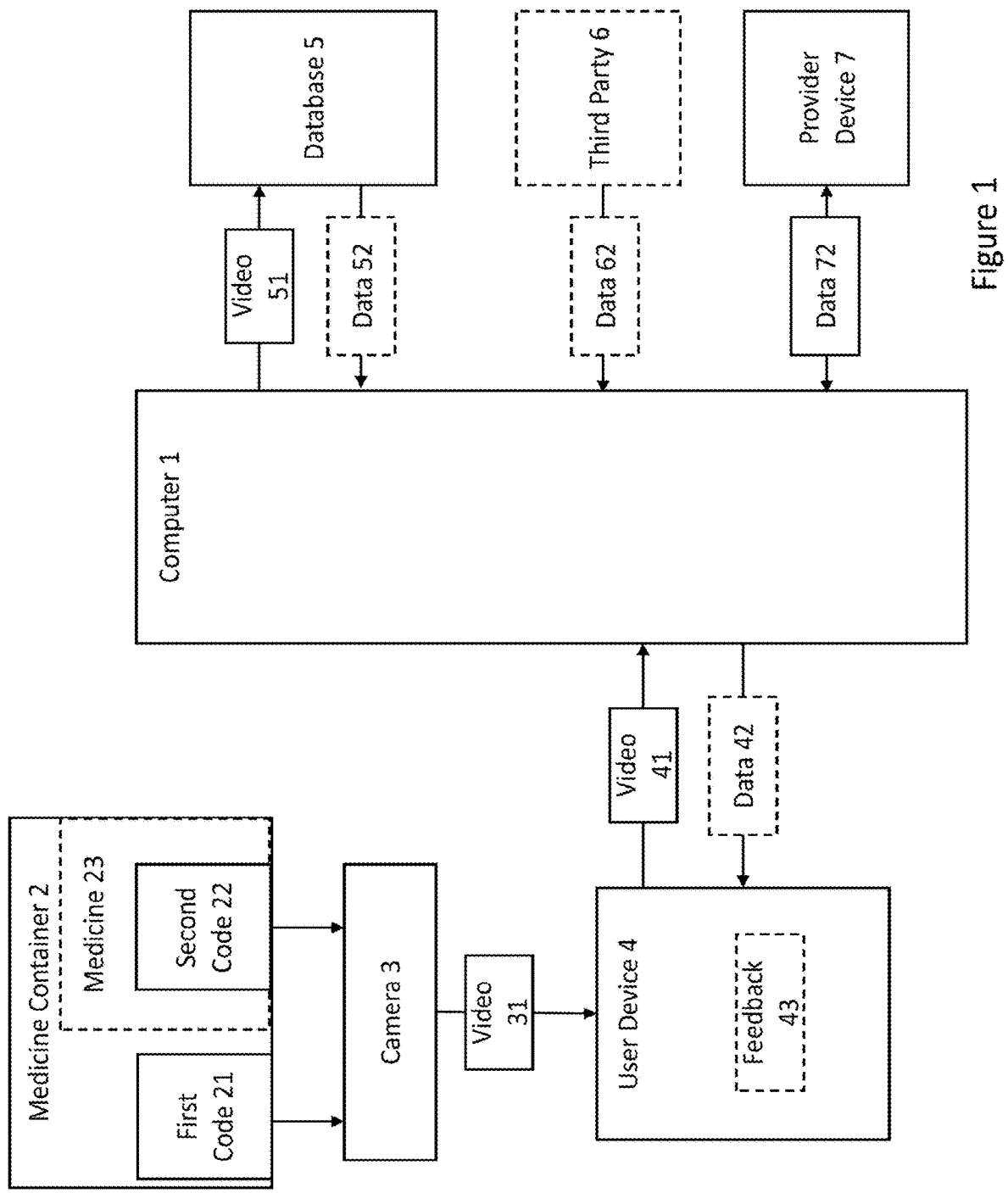
FIG. 1 is a schematic diagram depicting one embodiment of a system for monitoring drug delivery.

Referring to FIG. 1, shown is one embodiment of a system for monitoring drug delivery.

The system may include a computer 1. The computer 1 may be a processor, remote computer, computer server, network, a web server/app or any other computing resource.

The system may also include a medicine container 2. The medicine container 2 may have a first code 21 and a second code 22. The first code 21 may be on the outside of the medicine container 2 and may be visible before being opened. The second code 22 may be inside the medicine container 2. The second code 22 may not be visible, readable, or otherwise knowable until the medicine container 2 is opened.

The system may also include a camera 3. The camera 3 may be a webcam, a phone camera, a laptop camera, or other camera, capable of recording videos.

The computer 1 may be in data communication with a user device 4. The user device 4 may be a computer, laptop, smartphone, tablet or other electronic device capable of transmitting and receiving data. The camera 3 may be in data communication with the user device 4. The camera 3 may be a part of or separate from a user device 4.

The computer 1 may be in data communication with a database 5. The database 5 may be a storage drive or array accessible to computer 1, cloud storage, a web-based storage system, or other means for storing data. The database 5 may send data 52 to the computer 1 or the computer 1 may retrieve data 52 from the data base 5. The database 5 may store information regarding the system, including the information discussed below. The database 5 may include one or more databases.

The computer 1 may be in data communication with a third party 6. The third party 6 may be a storage drive or array accessible to computer 1, cloud storage, or another computer.

The computer 1 may be in data communication with a provider device 7. The provider device 7 may be a computer, laptop, smartphone, tablet or other electronic device capable of transmitting and receiving data.

The first code 21 and the second code 22 may be any, one-, two-, or three-dimensional code capable of storing data although not limited thereto. For example, a one-dimensional code may be a barcode, a two-dimensional may be a QR code, and a three-dimensional code may be a 3D array. The system may include as many codes as necessary and is not limited to the first code 21 and the second code 22.

Medicine 23 may be inside the medicine container 2, although not limited thereto. The medicine 23 may be in any container such as a bottle, pill pouch, package, syringe, canister, or other container for housing medicine. The second code 22 may be affixed to the medicine 23 or the container of the medicine 23.

The medicine package 2 and the medicine 23 may be patient-specific and/or dose-specific. The medicine package 2 may be single use. The medicine package 2 may be reusable and the first code 21 and the second code 22 may be reprogrammable.

In one embodiment the medicine container 2 may be a single-use liquid medicine vial. The medicine container 2 may be made tamper aware through the first code 21 which may be a single use barcoded security label.

The camera 3 may record pictures and/or a video 31. The video 31 may be received by the user device 4. The video 31 may contain images of the first code 21 and the second code 22. For example, the video 31 may begin with the user showing the first code 21 on camera, the user may then proceed to show the second code 22 on camera.

In one embodiment the user may be asked to speak a verification phrase during the video 31 such as "the brown fox jumped over the lazy dog". The verification phrase may add an extra layer of security to the video 31 by requiring audio in the video 31 and requiring the user to make oral movements after taking an oral medication, although the reason for the verification phrases is not limited thereto. The verification statement may be in addition to or instead of either the first code 21 and/or the second code 22. For example, the video 31 may contain images of the first code 21 and the verification phrase but not the second code 22, or any combination of the first code 21, the second code 22 or the verification statement, although not limited thereto.

The camera 3 may switch between multiple views if available. For example, on a smart device with a rear camera and a front camera the camera 3 may switch between the camera views as needed. This switch may be manual, automatic, or prompted to the user, although not limited thereto.

The camera 3 may be configured such that once video 31 has begun being recorded, the recording may not be stopped and restarted.

The user device 4 may provide feedback 43 to the user providing confirmation that the video captured the first code 21 and the second code 22. The feedback 43 may be a sound such as a beep, a vibration, a flash of light such as a camera flash or strobe, or a notification pop-up, although not limited thereto. For example, the notification pop-up may be a snackbar pop-up or a notification bar that appears on the sides of a smart device.

The feedback 43 may also be an alert or prompt directing the user to perform an action. For example, feedback 43 may notify the user that there is insufficient lighting, the first code 21 or the second code 22 was not properly captured and should be shown again, the medicine package 2 should now be opened, the user should now take the medicine, the user's face must be fully shown when taking the medicine, the user must now speak a verification phrase, and/or the user may end the recording, although not limited thereto.

The computer 1 may receive the video 41 from the user device 4. The video 41 may contain metadata. The metadata may be a user account, a video name, a time stamp of video generation or a time stamp of receipt by the computer 1. The metadata may also include the first code 21, the second code 22, or any other identifier that would identify the medication.

The video 41 may be uploaded continuously, in segments, in real time as the video is recorded, or by any other upload style capable of transferring data. For example, if the user device 4 loses connection to the computer 1 the upload of the video 41 will stop and resume once the connection is reestablished.

In one embodiment the video 31, 41 may be continuously recorded in real-time via a live stream. The video 31, 41 may be recorded and directly sent to the computer 1 bypassing the upload stage and any temporary/permanent storage on the user device 4. The live stream may be stored on the database 5 and/or monitored in real-time or at a later time by the provider device 7 or another authorized person.

In one embodiment the computer 1 may be accessible by the user device 4 through a web application. The web application may be downloaded on the user device as a mobile application, or it may be a web browser application, although not limited thereto. The user device 4 may navigate the web application and may access information such as a list of previously recorded dosage periods, medication information, clinic and clinician contact information, account settings, dosage regime data, recording instructions, and mock recording practice, although not limited thereto. The provider device 7 may navigate the web application and may access information about a number of patients in the system. For example, the provider device may access the web application and review uploaded dosage videos from a plurality of patients, review logs of recorded dosage periods and if there are any missed recordings/dosage periods, review and enter billing information, review metadata from an upload dosage period, and review and respond to messages from patients, although not limited thereto. The user device 4 and the provider device 7 may connect to each other through the web application, the devices 4, 7 may be connected whereby a patient and a clinician may communicate in real-time via video, voice, and/or text, screen sharing, among other forms of communication, although not limited thereto.

The video 41 may be compressed, in some cases to a size less than 5 megabytes. The video 41 may be converted using ffmpeg technology, although not limited thereto.

The computer 1 transmits the video 51 to the database 5 for storage. The database 5 may have additional firewall and authentication procedures to secure the video 51. For example, the database 5 may be a secure database having a firebase authentication service for HIPAA compliance and secure user and password management. In one embodiment the database 5 may be cloud based storage.

The computer 1 may transmit data 42 to the user device for display to the user. Data 42 may include information about the medicine container 2, medicine 23, if a video has already been recorded for the medicine dose period, links to external resources, or contact information, although not limited thereto. For example, when the camera 3 captures an image of the first code 21 or the second code 22, the computer may retrieve data 52 from the database 5 or data 62 from a third part 6 and transmit data 42 to the user device 4. The user device 4 may access a client-side dashboard whereby the user device 4 may request the aforementioned data from the computer 1. The computer 1 may query for the information from the database 5 and/or a third party 6 source and send the data 42 to the user device 4. The data 42 may be part of data 52 and/or data 62.

The user device 4 may display a list of recordings, which may be helpful for a user to remember if they already took medicine for a specific dosage period. The user device 4 may display contact information for the user's care provider for further assistance or a link to the medicine manufacturers website.

The system may contain a reader in data communication with the user device 4. The reader may be a NFC reader, a magnetic sensor, or any other sensor capable of close-range receipt of data. In such an instance, the first code 21 and second code 22 may be a tag on the outside of the medicine container 2. The tag may be a tamper-evident NFC code. For example, the reader may scan the tag and receive information about the medicine, dosage regime, and whether a video should be recorded, although not limited thereto. The same tag may be scanned additional times providing the same or different data, such as additional user prompts and/or steps for the user to perform while recording the video, although not limited thereto.

In one embodiment the computer 1 may have software executing on it to analyze the video 41. The software may include machine learning algorithms which may automatically detect and track objects appearing in the video 41. The machine learning algorithms may also detect noises in the video 41.

For example, machine learning algorithms may detect and track the first code 21, the second code 22, the medicine container 2, the medicine 23, the user's face, the user's hands, noises and/or other elements in the video 41. The detecting and tracking may occur in real time as the video 41 is being received by the computer 1. Alternatively, the computer 1 may receive the video 51 previously uploaded to the database 5 as data 52 to be analyzed.

The computer 1 may record metadata if it is determined that the medication dosage regime was not followed, was tampered with, or if the video 41 contains other suspicious behavior. Suspicious behavior may be predetermined by the computer 1 based on previous recordings or a third party such as a medical care provider although not limited there to. The computer 1 and/or machine learning algorithm may have artificial intelligence (AI) modules to perform reliable auto flagging. The computer 1 and/or machine learning algorithm may rely on factors such as medicine container 2 movement, hand and facial movement, time taken between scanning the first code 21 and/or the second code 22, overall video time among other factors to determine if a session should be flagged for further review. The computer 1/machine learning algorithm may also use event interpretation whereby tracking the position and movement of objects in the video, as described above, the system may be able to interpret the events in the video (i.e., the movement of the medicine container, users face, and hand indicate the user took the medicine or the position of the medicine container was not visible for a duration of the video and therefore there is a high chance the user did not take the medicine). A score may be determined for the video based on the tracking, which may be recorded in the metadata. Different weights may be given to various factors and the computer 1/machine learning algorithm may flag a missed consumption event.

Using event interpretation, the computer 1/machine learning algorithm may be able to detect and automatically complete tasks in the dosage period video. For example, the user device may prompt the user to take the medicine, once the user has taken the medicine the user may manually confirm that the medicine has been taken to proceed to the next step. The computer 1/machine learning algorithm may detect the movement and position of the users face and hand, the medicine container, and the medicine and determine that the user has taken the medicine, automatically completing the task without the user's manual confirmation.

The computer 1/machine learning algorithms may also flag other suspicious behavior such as video feed cutting out or inconsistencies in behavior or other factors between videos from the same user. For example, the machine learning algorithms may detect sources of noise, variations in pill color, shape, size, lighting, positioning, background, and foreground and compare these factors to previous videos taken by a user. The computer 1/machine learning algorithm may also compare the user video to control videos and data. Based on the comparisons the computer 1/machine learning algorithm may determine a score for the video recorded in the video metadata and may flag the video for further review.

The computer 1/machine learning algorithms may, depending on the weighting and/or frequency of monitored factors and events, assign a different priority to the flagging and call for different action from the clinician or other manual reviewer.

The computer 1/machine learning algorithms may also be compatible with sublingual tablet and film used in buprenorphine-based OUD treatments. The computer 1/machine learning algorithms may use a neural network model to classify images of pills using machine learning algorithms. The system may be compatible with predeveloped machine learning algorithms, for example TensorFlow.js. The computer 1/machine learning algorithms may use placebo sublingual films with controlled participants taking photos using the camera on their device to create a standard for future comparison by the system. The computer 1/machine learning algorithm may receive these training images uncleaned, and thus will contain realistic sources of noise, variations in pill color, shape, size, lighting, positioning, background, and foreground, although not limited thereto. In a preferred embodiment a dataset of at least 520 images will be manually reviewed and classified, and approximately 104 training images will be used to test the model. The computer 1/machine learning algorithm may achieve an accuracy rate of at least 80% in identifying proper dosage regimes. The use of a larger data set of images may allow the system to achieve a greater accuracy.

The neural network model used by the computer 1/machine learning algorithms may be trained using a cloud computing platform, which may use HIPAA-compliant security measures. The system may be compatible with predeveloped cloud computing platforms, for example Google Cloud Platform.

The computer 1/machine learning algorithms may also perform automated identification of medicine vials in the video stream. The same process used to train the computer 1/machine learning algorithms model to recognize pill base medicine may also be used for training of vial identification. The vial may also be defined by its location and extent in a single frame and in every frame that follows, the computer 1/machine learning algorithms may determine the object's location and extent or indicate that the object is not present.

In an exemplary embodiment the machine learning algorithms may be incorporated into the submission review process in two ways. The submission may be initially flagged for priority clinician review. This initial flagging may be generated based on the output of object detection algorithms evaluating a recorded submission. Objects detected may include, but are not limited to, the patient's face, a medication, and/or paraphernalia used in the administration of the medication. The submission may be further flagged for priority clinician review by comparing a given submission with a machine learning model built on historical data describing submissions that were "Accepted" and "Rejected". "Accepted" and "Rejected" submission may refer to submissions from the patient, submissions from another patient on the same or similar medication regime, and/or training submissions, although not limited thereto. The "Accepted" and "Rejected" submissions may be reviewed and mark by automatic or manual review. The machine learning algorithms may compare data from the "Accepted" and "Rejected" submission including, but not limited to, the duration of the submission, presence of object detection in the submission, duration of specific segments of the submission process, the timing of submission, and a patient's individual history of submissions.

By using the machine learning algorithm, the system may reduce or eliminate the need for manual review and may increasing patient autotomy and anonymity.

The system may also include a contingency management ("CM") system, based on the principles of operant conditioning, which may involve the application of positive reinforcement (e.g., monetary incentives) contingent upon behavior change. CM may be an efficacious psychosocial intervention for substance use disorders. CM may encourage health-related behavior change, including treatment engagement and attendance, medication adherence, and abstinence from substance use. CM may rely on several key principles of operant conditioning including objective verification that the treatment goal has been achieved, timely delivery of the reinforcement, and sufficient magnitude of the reinforcement to be effective. Therefore, CM may require frequent monitoring of behavior change and variation in the delivery, magnitude, and kind of reinforcement. CM may utilize mobile-based healthcare interventions that deliver CM remotely, enabling greater access and ease of delivery, and perform significantly better than control conditions.

CM may integrate probabilistic prize-based incentives (e.g., a "loot box") to encourage adherence to dosage regimes. The CM integration into the system may, after each successful and timely recorded and uploaded dosage period, reward the user with an inventive (i.e., a "loot box"), which can be opened for an instant monetary prize (e.g., an Amazon gift card). The prize may be revealed after a short animation of the container opening. By way of example the prize may be probability rewards as follows: 50% of draws yielding a prize worth $1 USD, 41.8% $5 USD, 8% $15

USD and 0.2% $50 USD, although not limited thereto. The probability, magnitude, and kind of prize may vary depending on consecutive completed dosage regimes, patient information, feedback on incentive effectiveness from user and focus groups among other feedback providers, third party needs, the needs of key stake holders (patients, providers, and payors, among others) or any other factor that would impact the probability and reward of the positive reinforcement CM system. It is understood that the incentive type, amount, and delivery may vary depending on the needs of the user and the above is an exemplary discussion of one embodiment of the present invention.

Figure 2:
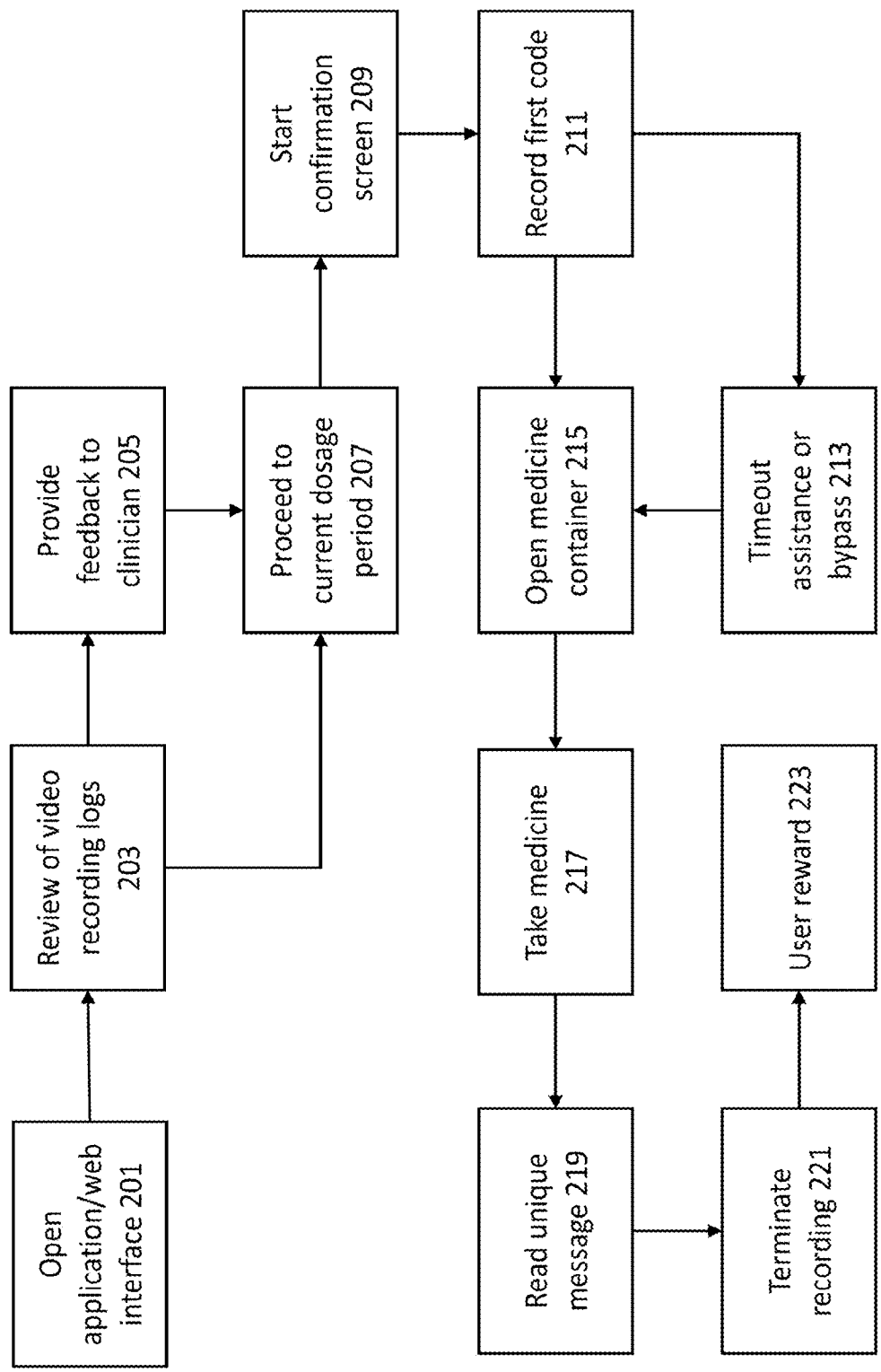
FIG. 2 is a flow chart depicting one embodiment of a system for monitoring drug delivery.

Referring now to FIG. 2, shown is a non-limiting exemplary flowchart of how a user may use the above-described system.

The user may open an application 201 on the user device 4, for example a smart phone, and access their care provider account, the access may be via login information, a single-use access code, client specific information associated with the user device 4, or another way to identify a specific user. For example, the application may be a stand-alone application downloaded on the user device or may be an internet browser application and the application is a web interface on a website, although not limited thereto.

The user may review video logs 203 of previously recorded/uploaded dosage periods if they have uploaded a video 41 for this medicine dose period. The computer 1 may retrieve data 52, for example video recording logs, from the database 5 and transmit this information as data 42 to the user device 4.

The user may review the video recording logs and notice that a previous dosage period was missed and/or not recorded. The user device 4 may prompt the user to provide feedback to a clinician 205, for example preset answers or a text field prompting the user to explain the missed dosage period. The user's response may be stored on the database 5 for review by a clinician, medical provider, or other third party, although not limited thereto. The user may then proceed to the current dosage period 207.

The user may see they have not already uploaded a video 41 for this medicine dose period. The user device 4 may display feedback 43, for example a message asking if the user would like to record a video of the medicine dose period. In one embodiment the user may see they have already uploaded a video 41 for this medicine dosage period. In this embodiment the user may be prevented from recording and uploading a new video 41 or the user may upload an additional video 41. The system may flag the videos for further review by a clinician, medical provider or other third party, although not limited thereto. If the user believes there is an error, the user device 4 may prompt the user to provide feedback to a clinician 205, for example a dialogue box prompting the user with preset answers or a text field to explain why there is already a video uploaded for a specific dosage period. The provided feedback may be stored and reviewed by a clinician, medical provider, or other third party, although not limited thereto. The user may then proceed to the current dosage period 207.

The user device 4 may display a recording start confirmation screen 209. The start confirmation screen 209 may provide user instructions such as "make sure you are in a well-lit room", "do not remove seal on medicine container until instructed", "the recording cannot be stopped or paused once started" and/or "secure your recording device as you will require both hands during the recording" although not limited thereto. The instructions may vary depending on the medicine, user, and/or provider although are not limited thereto.

The camera 3, for example, a smart phone camera having a front camera and a rear camera, may begin recording video 31 once the user confirms they are ready to record the dosage period video. The user will attempt to record the first code 211, for example a barcode or a QR code, affixed to the medicine container 2 on video using the camera 3. The user device 4 may give feedback 43, for example a beep, to the user that the first code 21 was successfully recorded on video. The user may then open the medicine container 215 breaking the seal and/or the first code 21 in the process.

In one embodiment the system contains a second code 22. The user may then open the medicine container 215 and remove the medicine 23 and second code 22. The user will attempt to record the second code 22, for example a barcode or a QR code, associated with the medicine 23 on video using the camera 3. The user device 4 may give feedback 43, for example a beep, to the user that the second code 22 was successfully recorded on video.

The user device 4 may provide feedback 43 that the code was not scanned properly and offer assistance 213 if the first code 21 and/or the second code 22 was not properly captured within a set time. The feedback 43 may be instructions on lighting, angle, or other factors to permit proper capture of the codes 21, 22. Alternatively, the feedback 43 may be an option to bypass 213 the scanning step and proceed with the dosage period recording. In one embodiment the user is given a set time to capture the code 21, 22 after which time the dosage period recording automatically proceeds to the next step.

The user may then record themselves ingesting the medicine 217. The user may be instructed to face the camera 3 and/or angle themselves towards the camera 3, show the medicine and place the medicine in their mouth. Once the user takes the medicine, the user device 4 may give feedback 43, for example a message instructing the user to say a unique message out loud 219. The unique message may verify that the user has ingested the medicine. The user device 4 may display an end recording button for the user to terminate the recording 219 once the user says the verification statement, ending the video 31.

The user device 4 may receive the video 31 and may add metadata, for example a time stamp of when the video was recorded, to the video 31. The computer 1 may receive the video 41 from the user device 4.

The computer 1 may store the video 51 on the database 5. A care provider may access the video 51 from the database 5 to monitor user adherence to medication dosage regimes.

In one embodiment once the video 51 is uploaded to the database 5 a reward may be given to the user. The reward may be automatically sent/credited to the user or there may be a reward animation/reward procedure, although not limited thereto.

Figure 3A:
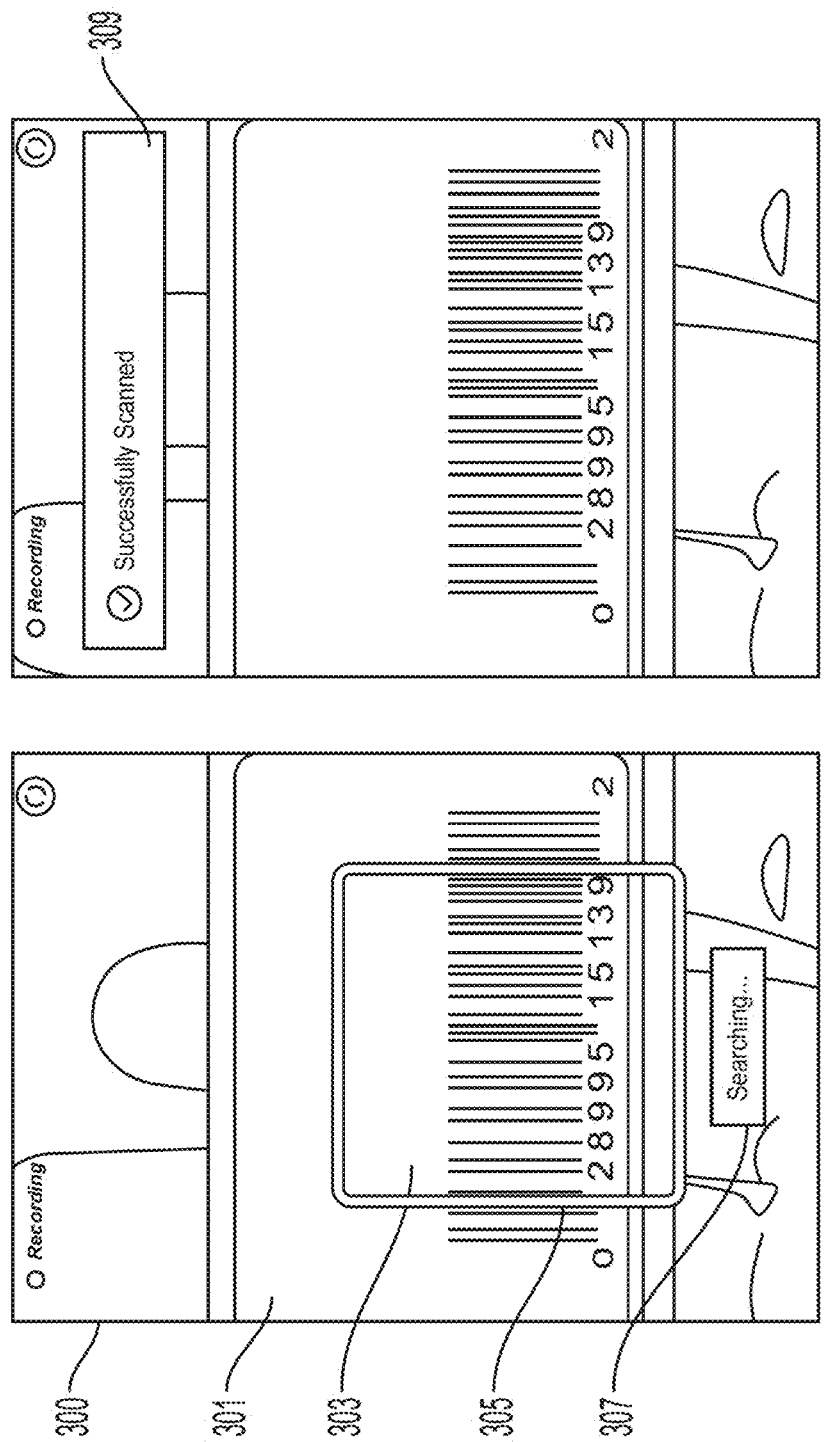
FIGS. 3A-C are diagrams depicting one embodiment of the code scanning process of a system for monitoring drug delivery.
Figure 3B:
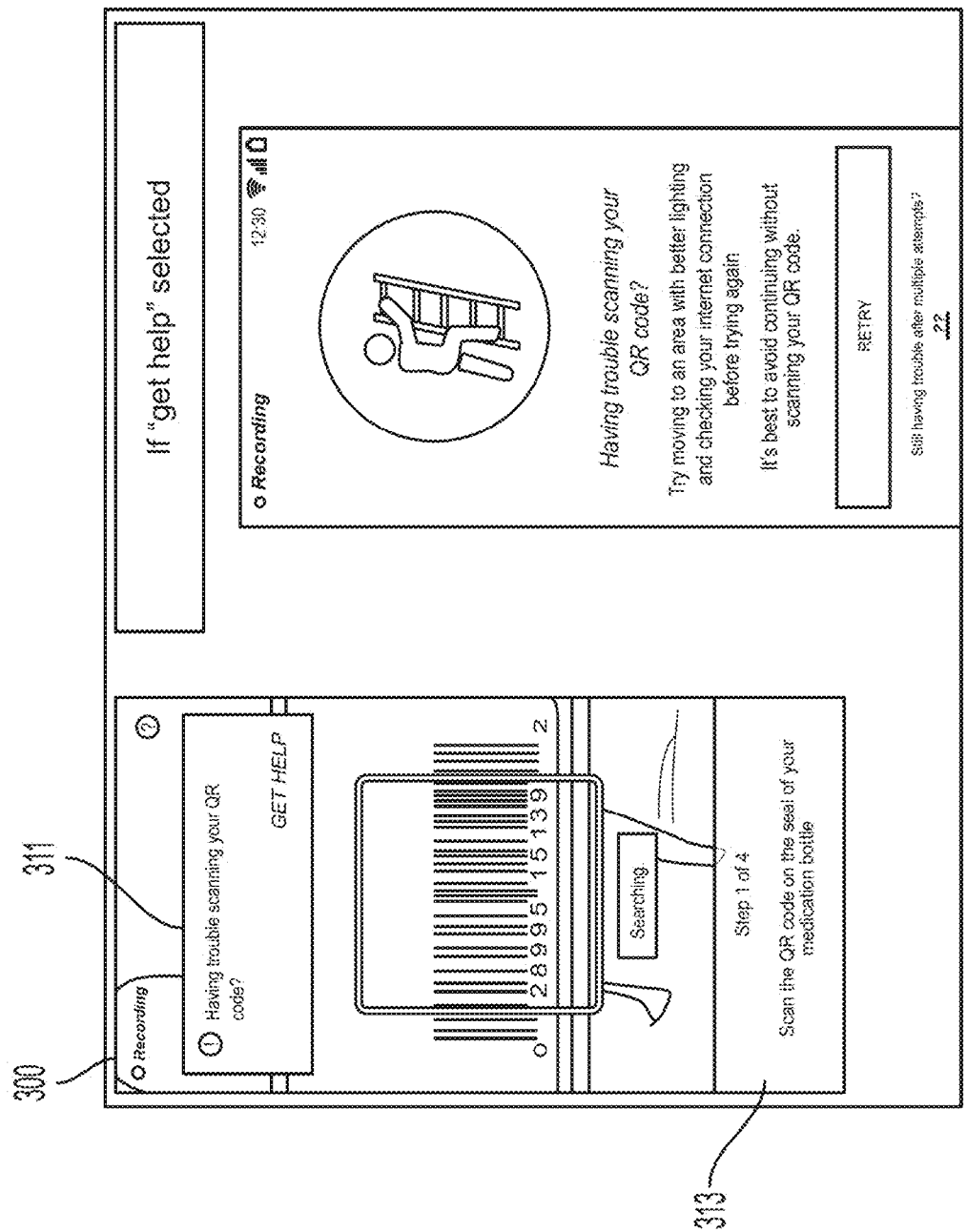
Figure 3C:
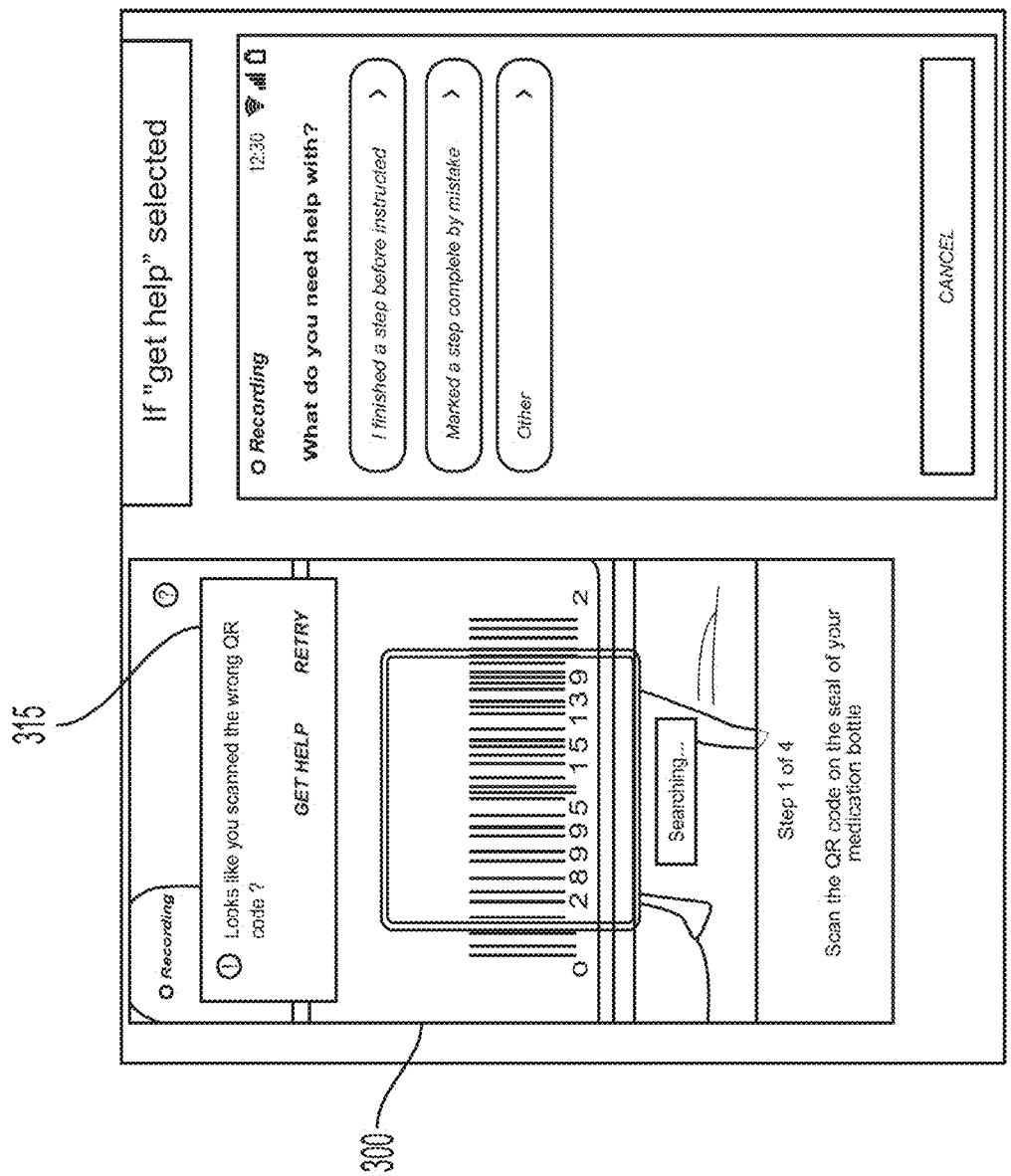

Referring now to FIGS. 3A-C, shown are non-limiting exemplary diagrams showing the scanning of a code in a system for monitoring drug delivery according to the present teachings.

As shown in FIG. 3A the user may see a preview 300 of the video being captured on the screen of the user device. In one embodiment, when the code on the medicine container is being captured on video the preview 300 displayed to the user may vary whereby a portion of the video preview may be greyed out or displayed in a darker color/filter 301 and the portion of the video capturing the code may be highlighted or displayed in a lighter color/filter 303. In one embodiment, the lighter/highlighted portion 303 may be a square or any other shape corresponding to the shape of the code although not limited thereto. The lighter/highlighted portion 303 may have a query indicator 305 which may be animated to move around the edge of the lighter/highlighted portion 303. The query indicator 305 may inform the user that the system is attempting to capture the code. The video preview 300 may also have a "searching" overlay 307 indicating to the user that the video is searching for the code, the "searching" overlay 307 may be animated showing that the system is still attempting to capture the code. Once the code is captured successfully the video preview 300 may display a notification that the code was successfully scanned. For example, the notification 309 may be a snackbar notification, although not limited thereto.

As shown in FIG. 3B the video preview 300 may display a notification 311 if the system encounters difficulties scanning the code. The notification 311 may be displayed while the video preview 300 has the highlighted 303 and/or darkened 301 overlays as shown in FIG. 3A and may be a snackbar notification, although not limited thereto. The notification 311 may display information to assist the user or provide a link to additional information, although not limited thereto. For example, the system may detect that the code is not being captured properly based on time elapsed since starting to scan the code or the position and/or movement of the code and/or medicine container, although not limited thereto. The system may then display notification 311 querying if there is "trouble scanning the code?" and providing a link to "get help". The link may provide information such as tips to capture the code, answers to common questions, potential bypasses if the code is unable to be scanned, and a return feature to retry capturing the code, although not limited thereto. The video preview 300 may also display a task indicator 313. The task indicator 313 may provide instructions, the name of the task, the number of tasks completed, the number of tasks to be completed, or additional information about the dosage video, although not limited thereto.

As shown in FIG. 3C the video preview 300 may display a notification 315 if the scanned code differs from the code the system was expecting. The notification 315 may be displayed while the video preview 300 has the highlighted 303 and/or darkened 301 overlays as shown in FIG. 3A and may be a snackbar notification, although not limited thereto. The notification 315 may display information to assist the user, provide a link to additional information, or provide an option to "retry" and attempt to scan the code again, although not limited thereto. The scanned code may differ from the expect code for a variety of reasons including the wrong medicine container for the dosage period being selected, the user manual completed a task before they were supposed to, or the image of the code wasn't clear, although not limited thereto. The notification 315 may provide a link to preset options explaining/providing solutions to common situations where the scanned code differs from the expected code and may provide an "other" option for the user to complete if none of the presets are responsive to the specific error.

Referring now to FIGS. 4A-E, shown are non-limiting exemplary diagrams of the user interface in a system for monitoring drug delivery according to the present teachings.

Figure 4A:
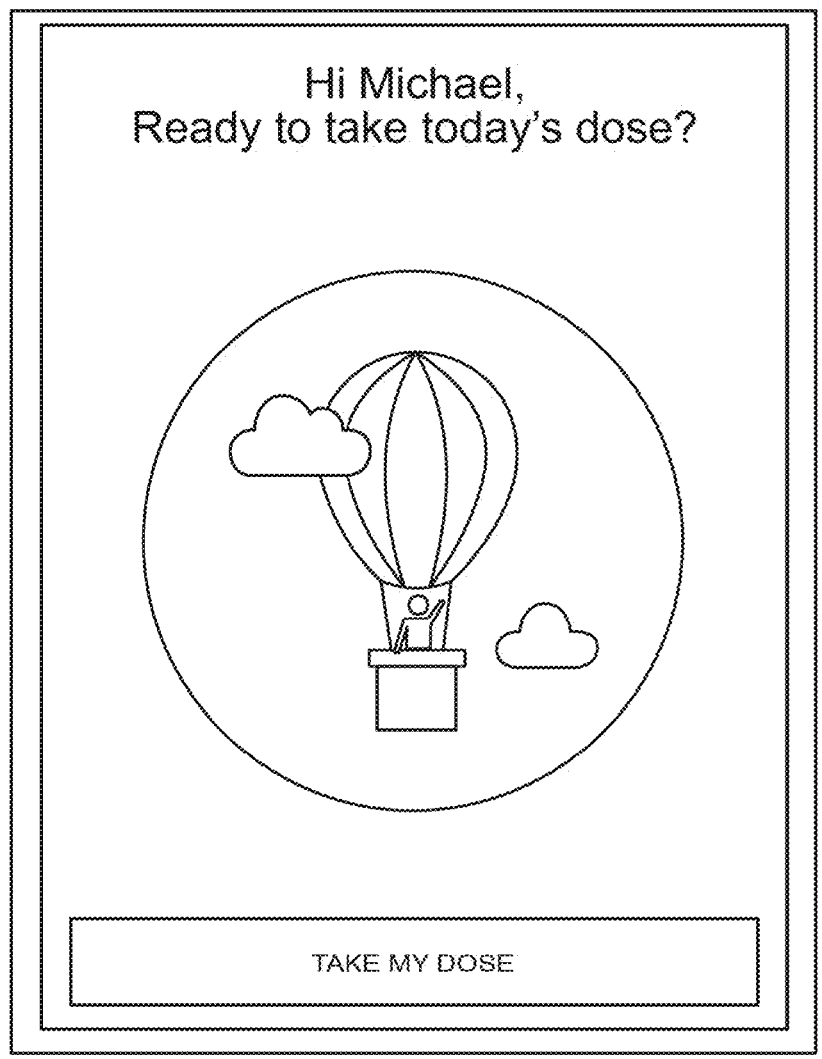
FIGS. 4A-E are diagrams depicting one embodiment of the user interface of a system for monitoring drug delivery.

Shown in FIG. 4A is a home screen. The home screen may be accessible once a user logs in or otherwise provides unique identifying information, such that the system knows which user and dosage period is being recorded. The home screen may display personal information about the user such as the users name, although not limited thereto. From the home screen the user may proceed to a confirmation screen.

Figure 4B:
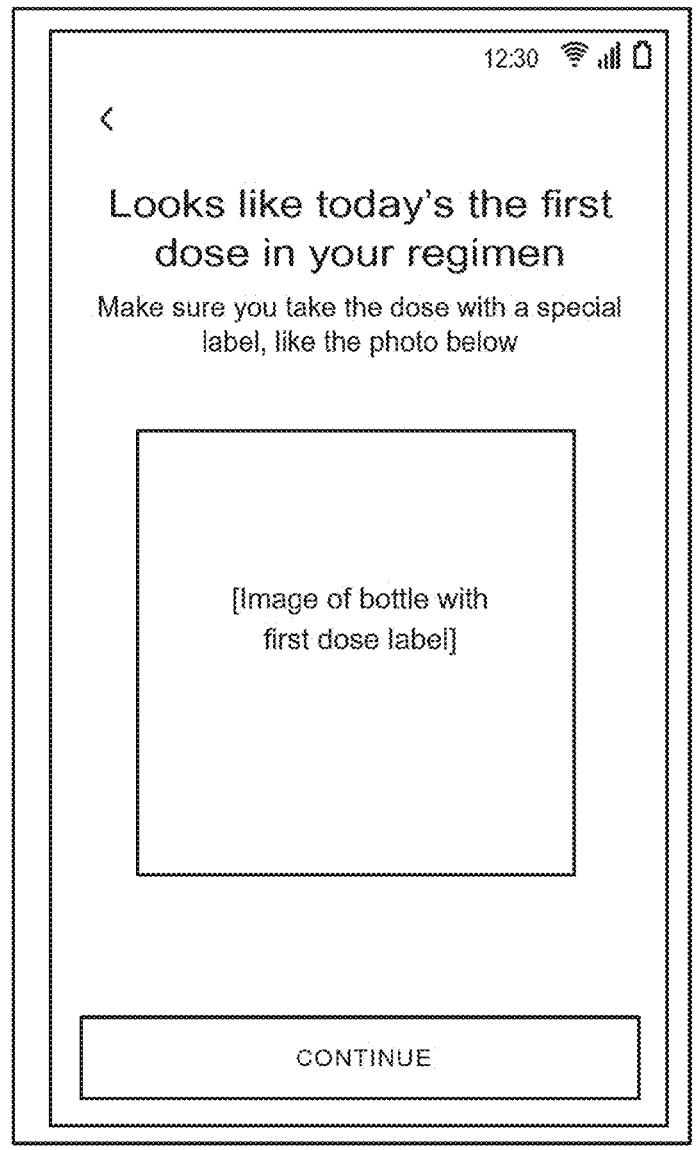

Shown in FIG. 4B is a confirmation screen. The confirmation screen may provide dosage period information including if this is the first dose in the regime, last dose in the regime, or current progress in the regime, although not limited thereto. The confirmation screen may display an image of the medicine and/or medicine container for the current dosage period in the dosage regime and provide a prompt to confirm the medicine/medicine container the user is going to take for the current dosage period matches the image. From the confirmation screen the user may proceed to a scheduling screen or navigate back to the home screen.

Figure 4C:
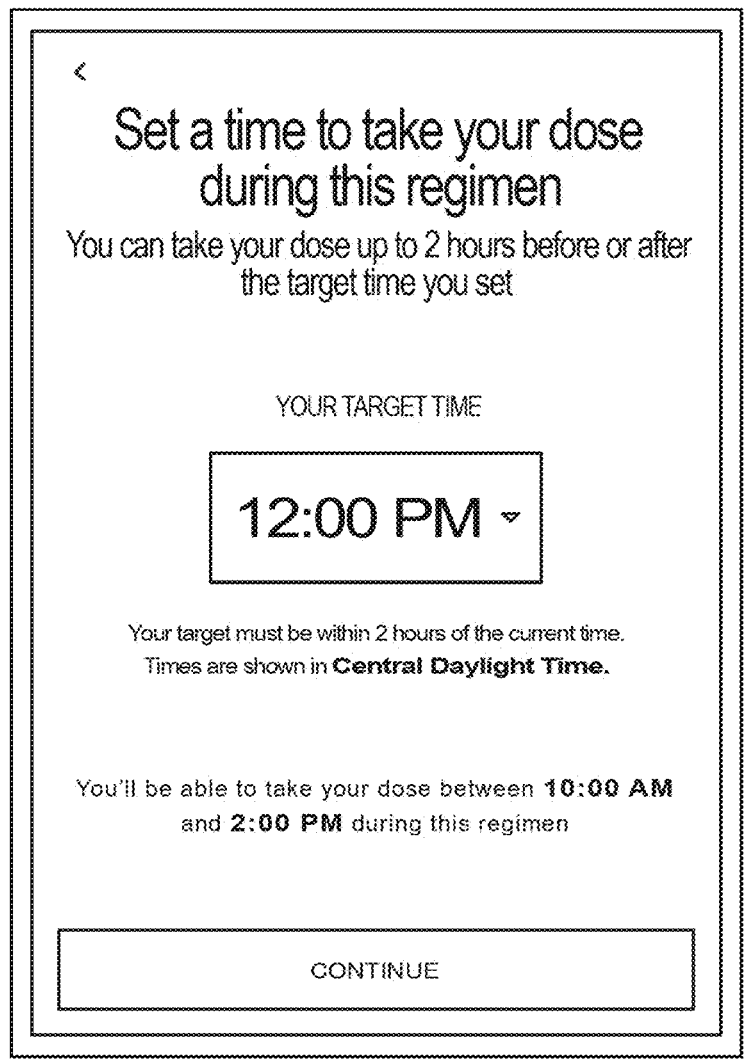

Shown in FIG. 4C is a scheduling screen. The scheduling screen may provide scheduling options to set a date and/or time for the dosage period. The date and/or time may be set by inputting a specific time, the use of a drop-down menu, or other known methods for selecting the date and/or time. The system may provide a preset window of time for the dosage period (e.g., two hours from the set dosage period) or the widow of time may be adjusted. The window of time for a dosage period may be adjusted manually or automatically and may vary depending on the medicine being taken, consumption track record of a patient, or other factors that would benefit a longer or shorted window of time for a dosage period. The system may prevent the video of the dosage period from being recorded or uploaded if the video of the dosage period is not within the scheduled window of time. The video of the dosage period may be flagged for further review if the recording is taken outside the window of time for the dosage period. From the scheduling screen the user may proceed to the instruction screen or navigate back to the confirmation screen.

The scheduling screen may also include a geographic location. The geographic location for the dosage period or dosage location, may be set using an address, a preset list of locations, by dropping a pin on a map, or other means for providing a geographic location. The system may provide a preset acceptable distance from the dosage location (e.g., 500 ft from the set dosage location) or the acceptable distance may be adjusted. The acceptable distance from the dosage location may be adjusted manually or automatically and may vary depending on the medicine being taken, consumption track record of a patient, or other factors that would benefit a longer or shorter acceptable distance for a dosage location. The user device may include a GPS, proximity sensor, or equivalent geographic locator, to monitor the location of the user device while the video of the dosage period is being recorded. The system may prevent the video of the dosage period from being recorded or uploaded if the video of the dosage period is not taken within the acceptable distance of the dosage location. The video of the dosage period may be flagged for further review if the recording is taken outside the acceptable distance of the dosage location. In an alternate embodiment the recording may be stopped, or a warning displayed to the user if the user device is leaving the acceptable distance from the dosage location.

Figure 4D:

Shown in FIG. 4D is an instruction screen. The instruction screen may provide instruction for recording the dosage period such as do not remove seal on medicine container until instructed, that the video may not be stopped or paused once started, to be in a well-lit room, to avoid recording in a crowded/noisy place, or to be the only person in frame, although not limited thereto. The instruction screen may also provide a link to more recording instructions and/or recording tips, which may be a written, audio, or video dosage recording walkthroughs although not limited thereto. From the instruction screen the user may proceed to the start recording screen or navigate back to the scheduling screen.

Figure 4E:
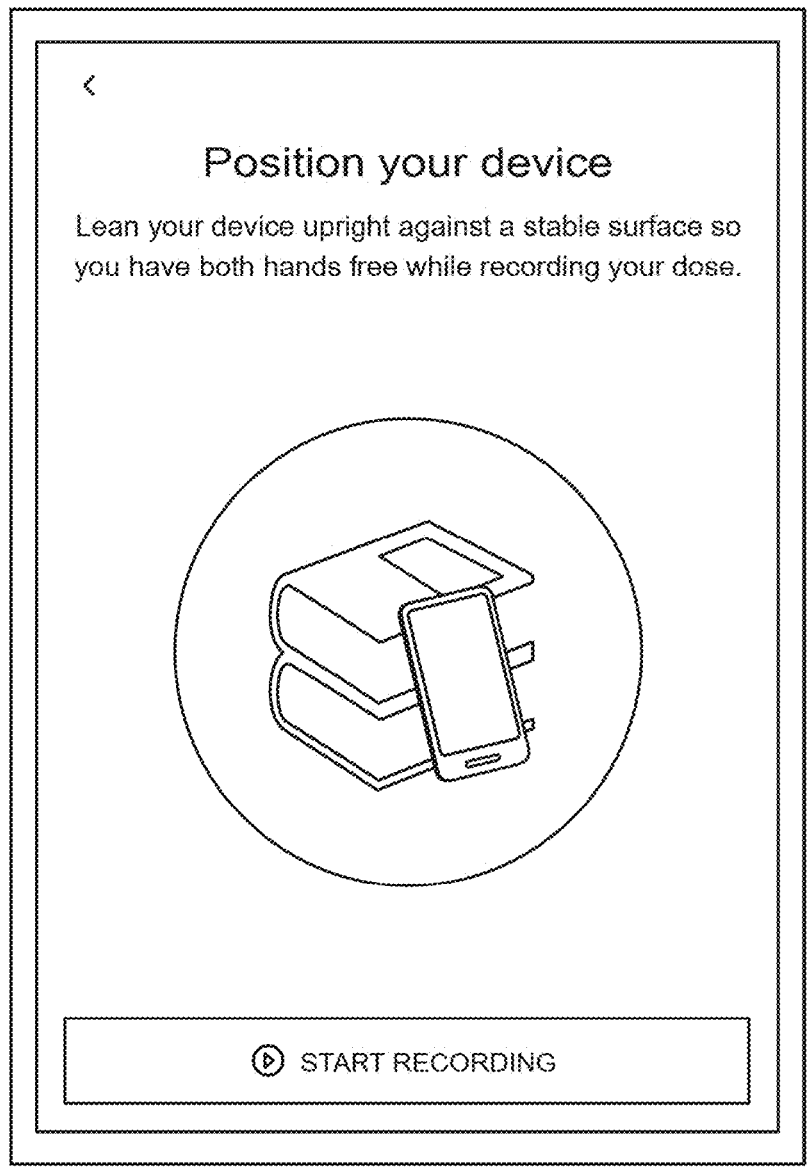

Shown in FIG. 4E is a start recording screen. The start recording screen may provide further recording instructions and a start recording button. From the start recording screen the user may navigate back to the instruction screen. In one embodiment once the start recording button is selected the dosage period video will begin recording, the video may not be stopped, pauser or restarted, and the user may no longer navigate back to the instruction screen.

It is understood that FIGS. 4A-E depict one example of the user interface according to the present teachings. The different features described in each screen are non-limiting and may be used in combination with other features, used in combination with features described in a different screen of the user interface, or split between multiple and/or additional screens. Furthermore, navigation between the different screens is described for the purpose of demonstration, it is understood that the navigation between screens is not limited to the linear navigation described and may be linear or non-linear and may be in any order.

Figure 5A:
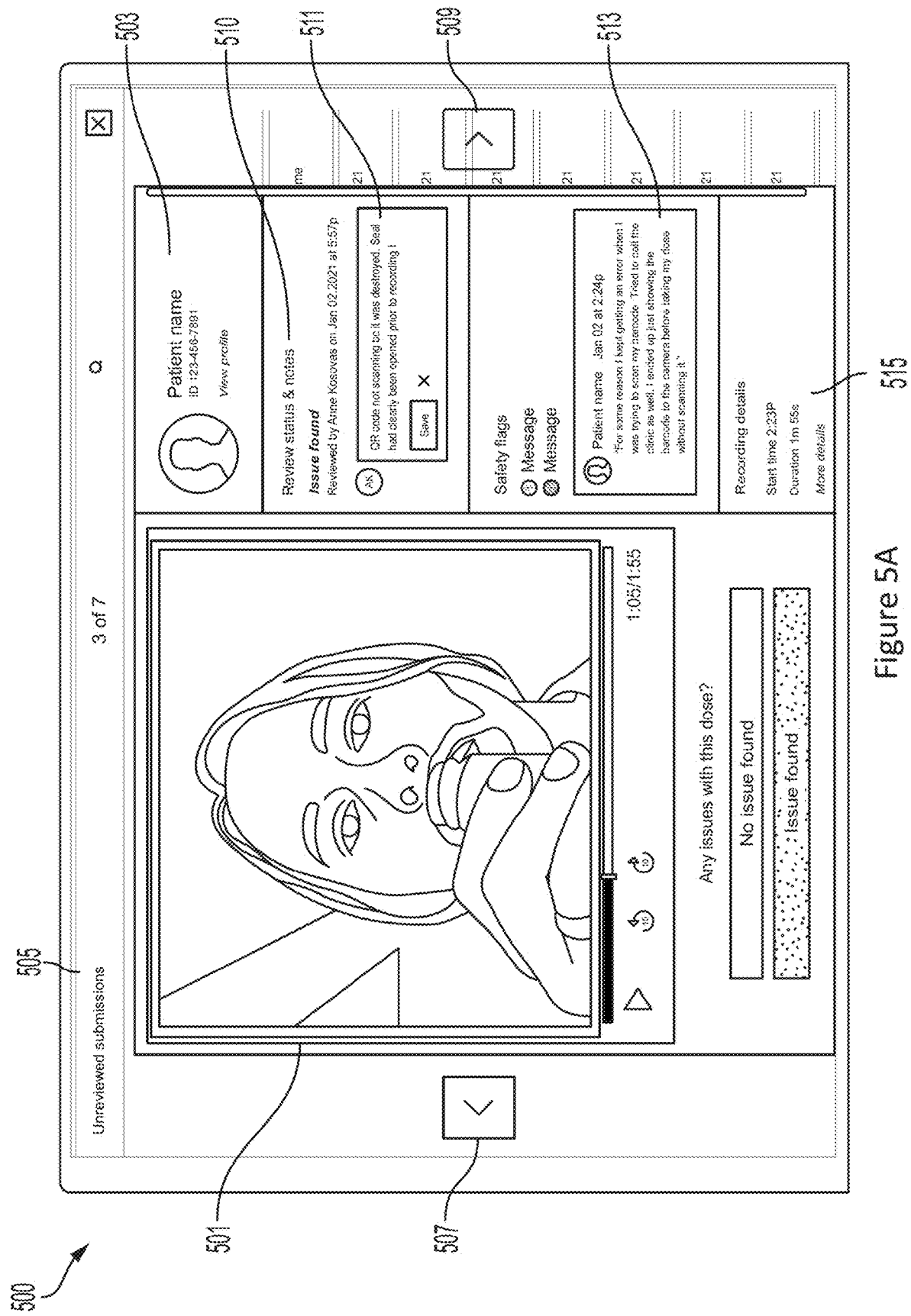

Referring now to FIG. 5A, shown is one example of the provider review interface in a system for monitoring drug delivery according to the present teachings.

The provider interface 500 may be a web-application, desktop application, mobile application, or other computing program. The provider interface 500 may be accessible by a mobile phone, desktop computer, laptop computer or other computing resource and may be downloadable or non-downloadable software.

The provider interface 500 may include a display 501 of a patient dosage period recording and identifying information 503 of the patient associated with the dosage period recording. The display 501 may include a progress bar of the video play back, a pause and play button, a fast forward and rewind button, a play back time, a play back speed, and other functionalities of video play back mediums. The identifying information 503 may include a patient name, patient picture, an id number, and other information associated with the patient, as well as a link to more detailed information, although not limited thereto.

The provider interface 500 may also include a progress indicator 505. The progress indicator 505 may display the current task in progress, for example unreviewed submissions, and the progress of that task, for example 3 of 7. The provider interface 500 may also include navigation buttons 507, 509 which may be used to change the submission being displayed on the provider interface 500. The submission being reviewed may be changed using the navigation buttons 507, 509, or by selecting from a list of submissions, although not limited thereto.

The provider interface 500 may further include review status and notes 510 of the dosage period submission. The review status and notes 510 may be reviewer comments 511, patient comments 513, or other notes associated with the dosage period submission from a manual or automatic reviewer. The review status and notes 510 may also include safety flags of varying degrees of severity. The safety flags may be manually input by a reviewer, automatically input based on preset conditions (i.e., the QR code did not scan properly) or based on machine learning algorithms.

The reviewer comments 511 may be from a previous care provider, physician, social worker, machine learning algorithm, or other authorized reviewer. The current reviewer may also write new notes and save them as reviewer comments 511. The reviewer comments 511 may be associated with a time stamp in the video.

The patient comments 513 may be submitted by the patient before, during, or after the dosage period recording. The patient comments 513 may be associated with a time stamp in the dosage period recording. A patient may be requested to submit additional patient comments 513 to be included in dosage period submission. This may allow suspicious event to be explained and creating a record of events.

The provider interface 500 may also include recording details 515 of the dosage period recording. The recording details 515 may be metadata of the video of the dosage period. The metadata may be a user account, a video name, a time stamp of video generation, a time stamp of receipt by the computer, or the length of the video, although not limited thereto. The recording details 515 may also include information about the scanning of the code and may include a link to additional details not initially displayed on the provider interface 500.

Figure 5B:
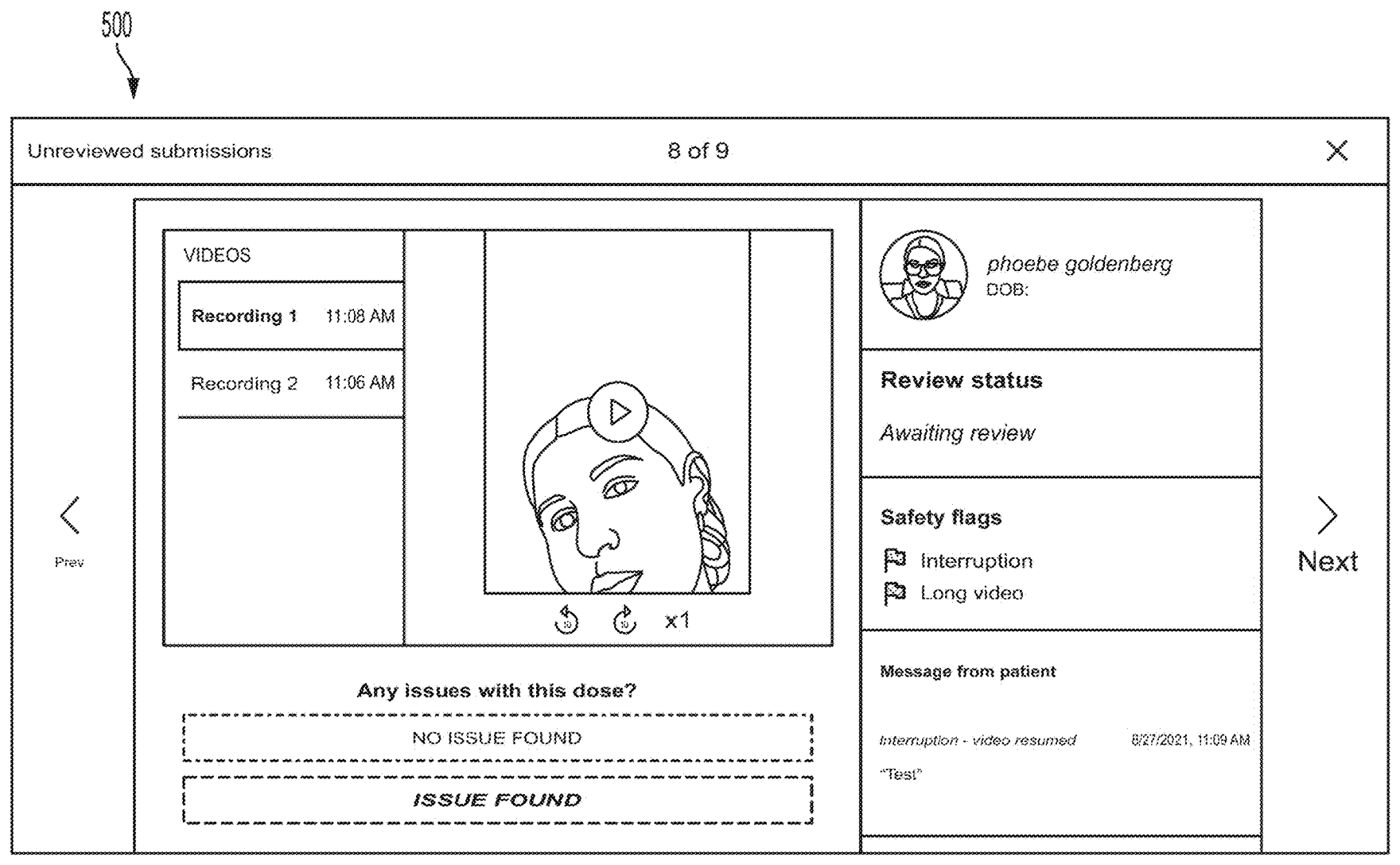

Referring now to FIG. 5B, shown is one example of the provider review interface in a system for monitoring drug delivery according to the present teachings.

The provider interface 500 may display multiple recordings. For example, the recording of the dosage period may be interrupted and be divided into two or more recordings. The multiple recordings may be displayed on the provider interface 500 and may be played back consecutively, simultaneously, or at different times. Each recording may be displayed with a duration and time of recording, although not limited thereto. The computer 1/machine learning algorithms may analyze and detect events and label which events in the dosage period were performed in each recorded segment. For example, the opening of a first and/or second label, taking of medicine, or speaking a verification phrase, although not limited thereto, may be marked as having occurred in a specific recorded segment.

The display may have a playback speed indicator to allow for faster or slower playback of the recordings. The speed indicator may adjust the playback speed of all the recordings simultaneously and/or independently.

The display may have a size indicator to allow for the recording to be displayed larger or smaller. The size indicator may adjust the size of all the displayed recordings simultaneously and/or independently.

Referring now to FIGS. 6A-F shown are examples of the provider management interface in a system for monitoring drug delivery according to the present teachings.

Figure 6A:

FIG. 6A shows an example of the provider management interface which may include an alerts page displaying patient alerts. The patient alerts may be messages from the patient or notifications from the system, although not limited thereto. The notifications from the system may include messages that a dosage period was not completed by a patient or that a dosage period was missed, although not limited thereto. The alerts may be color coded or sorted by other means to easily identify the type of alert. The alerts may include reference information about the patient, a description of the alert, and a date and time of the alert. The alerts may be searched or sorted according to patient name, patient birthdate, time received, type of alert, or other known methods of searching and/or sorting data. The alerts may be deleted, marked as complete, moved to a separate area (e.g., archived alerts), or saved for later review, although not limited thereto.

Figure 6B:
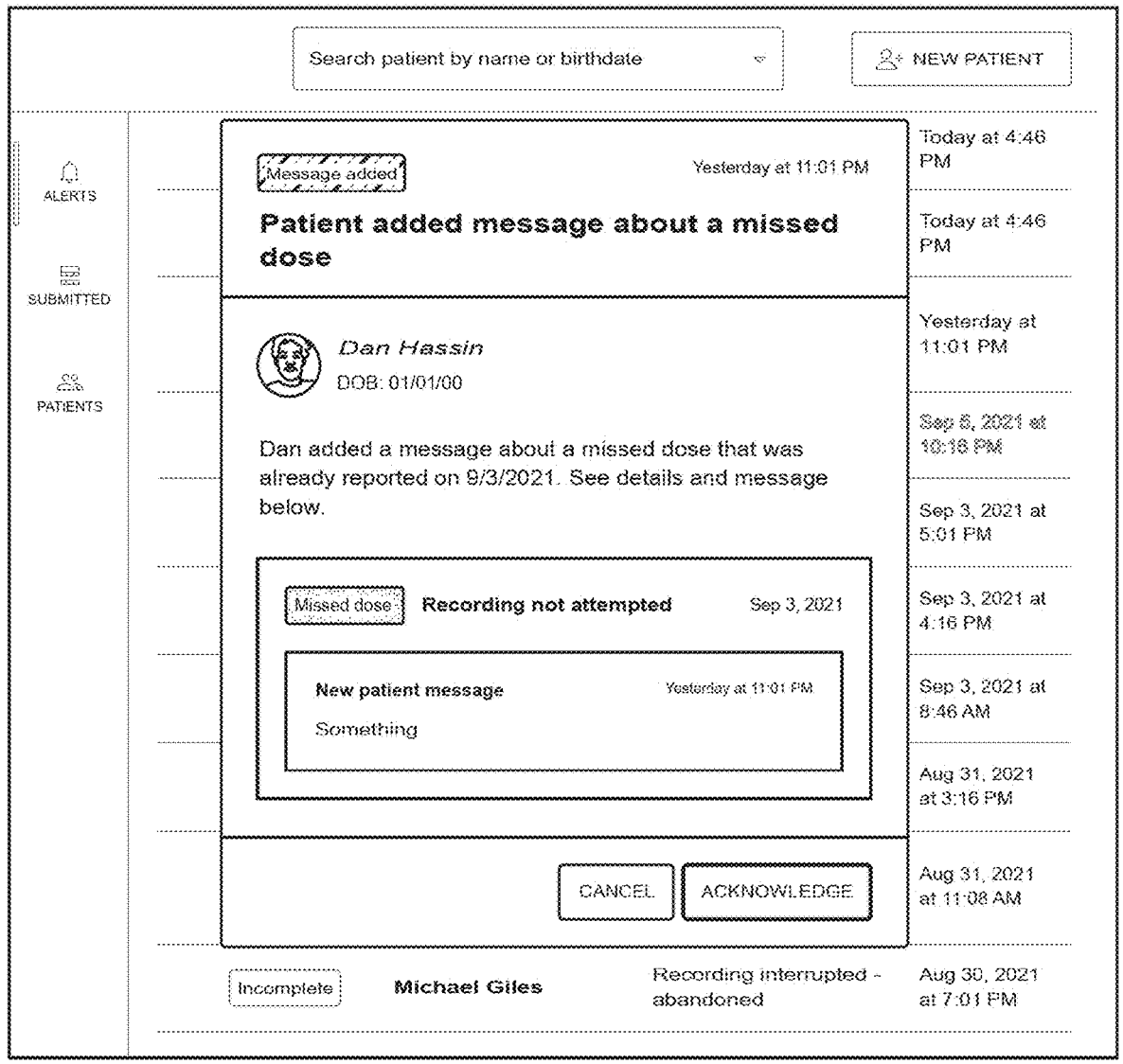

FIG. 6B shows an example of a report of one of the alerts. The report may include a patient name, date of birth, patient comments, patient photo, date and time of the alert, and related alerts and/or comments, although not limited thereto. The report may be canceled or acknowledged, although not limited thereto. Canceling the report may close the report for later review or delete the report and/or accompanying alert, although not limited thereto. Acknowledging the report may send a notification to the patient that the report was reviewed and acknowledge by the provider, mark the report in a patient's file, and/or delete the report and accompanying alert, although not limited thereto.

Figure 6C:
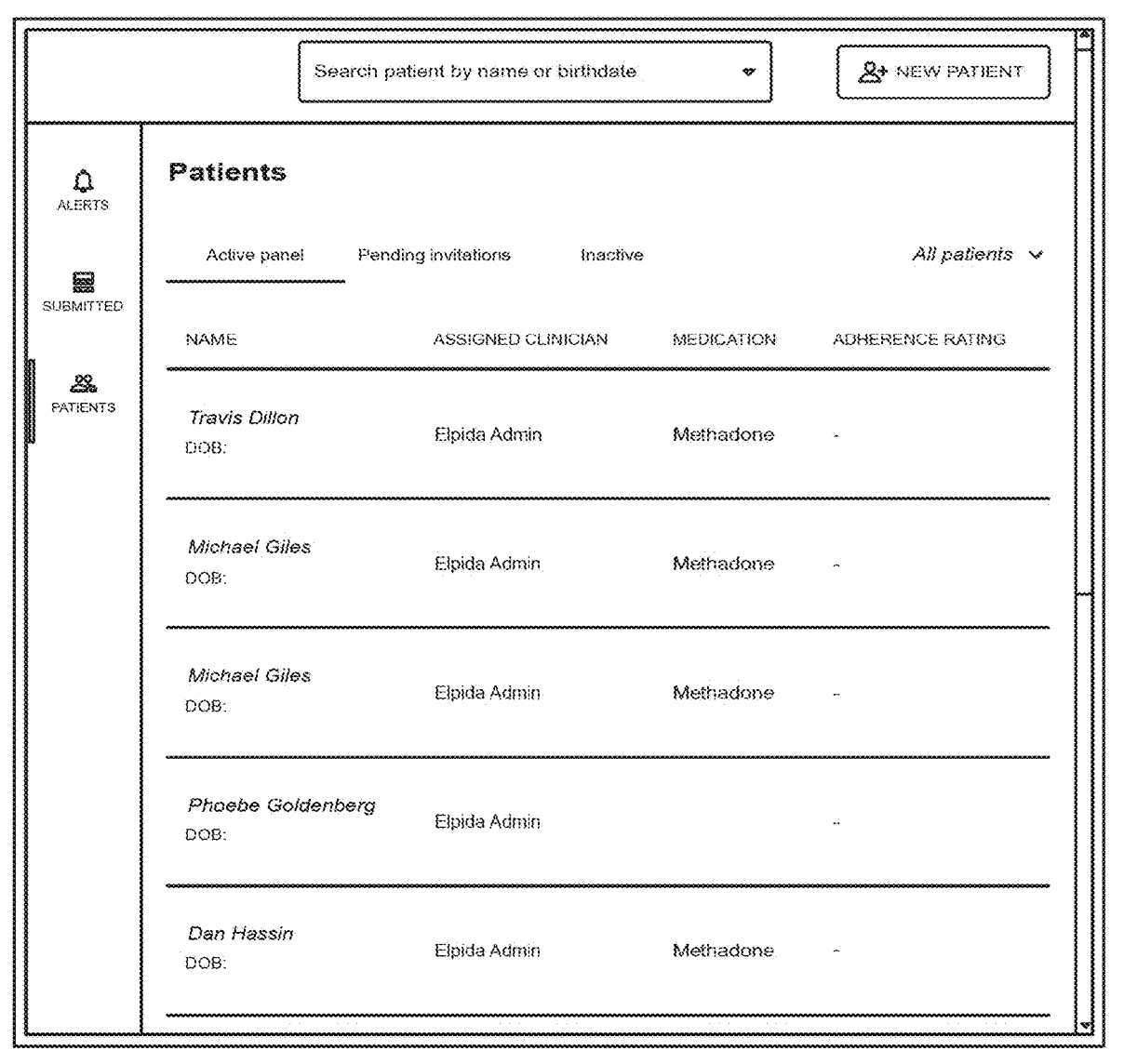

FIG. 6C shows another example of the provider management interface which may include a patients page. The patients page may include active patients, pending patients, and/or inactive patients, although not limited thereto. The patients page may display patient information including patient identifying information, an assigned provider/clinician, the medication regime the patient is on, and an adherence rating, although not limited thereto. The patient identifying information may include a patient name, date of birth, photo, and identification number, although not limited thereto. The medication regimen may include the type of medication the patient is taking, the dosage amount, or the frequency the medication is taken, although not limited thereto. The adherence rating may be calculated by the computer 1/machine learning algorithms based on patient compliance with a specified dosage regime and verification procedures.

Figure 6D:
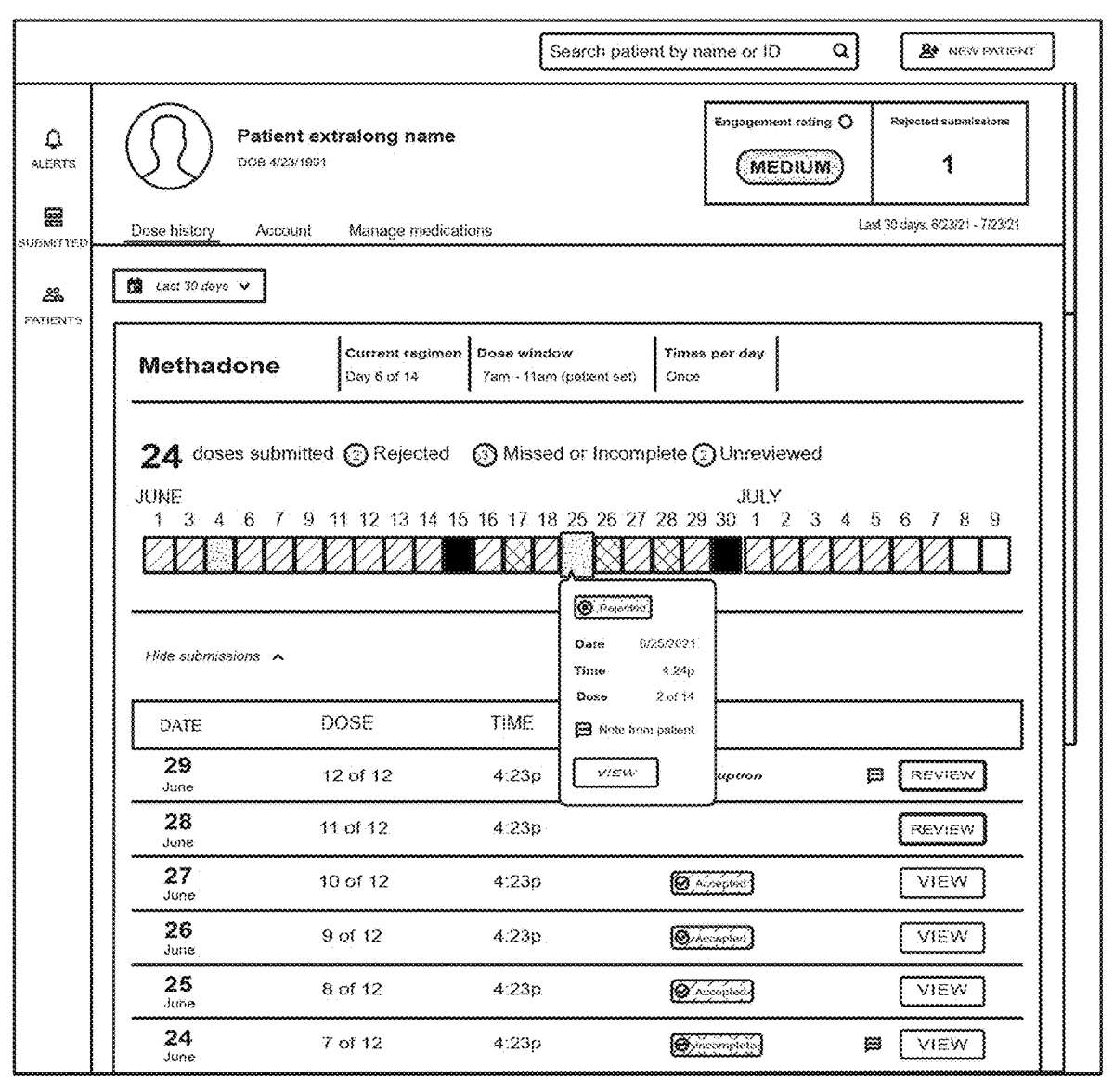

FIG. 6D shows an example of patient page which may include a dosage history page. The dosage history page may include identifying information about the patient, an adherence rating, number of rejected submissions, and dosage history. The adherence rating may be displayed as an engagement rating and may be calculated by the number of accepted, rejected, incomplete dosage periods, and provider specific input, although not limited thereto. The dosage history may be set to monitor a specific time period, e.g., the past day, week, month, year, all time, or between specific dates, although not limited thereto. The patient page may display dosage regime information such as medication, progress through the dosage regime, e.g., dose 6 of 14, dosage time window, and frequency of dose, although not limited thereto. The dosage time window may be a preset time frame, a patient set time frame, a provider set time frame, or any combination of the above, although not limited thereto. The dosage history may include a tally of the number of doses submitted and may include a further breakdown by accepted doses, rejected doses, missed/incomplete/other doses, and unreviewed doses, although not limited thereto. Each dosage period may include the date and time the dose was taken, the number of the dose, e.g., 2 of 14, notes/comments from the patient or provider, and the option to view the dosage period in greater detail, e.g., the provider review interface 500.

Figure 6E:
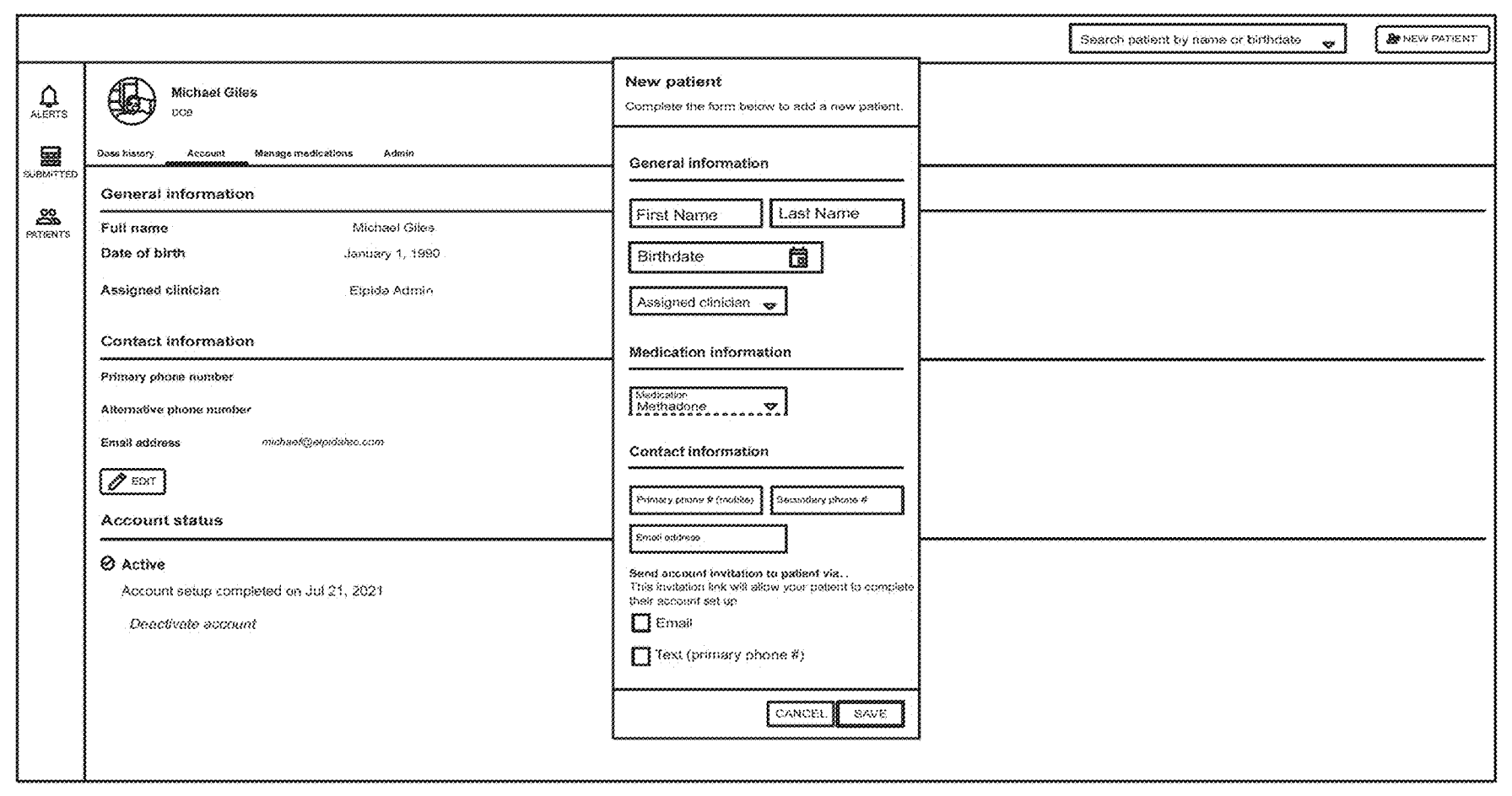

FIG. 6E shows an example of the patient page which may include an account page. The account page may include patient identifying information, patient contact information, e.g., phone number, email, emergency contact etc., and active status, although not limited thereto. The account page may be updated by the provider directly or by submission from the patient and may be updated manually or automatically.

The account page may also include the functionality to add a new patient. A new patient's identifying information, assigned provider/clinician, medication/dosage regime, and contact information may be filled out and added to the system for monitoring drug deliver. The new patient may be sent an invitation via email, text or other communication methods to complete their account set up and be added to the system.

Figure 6F:
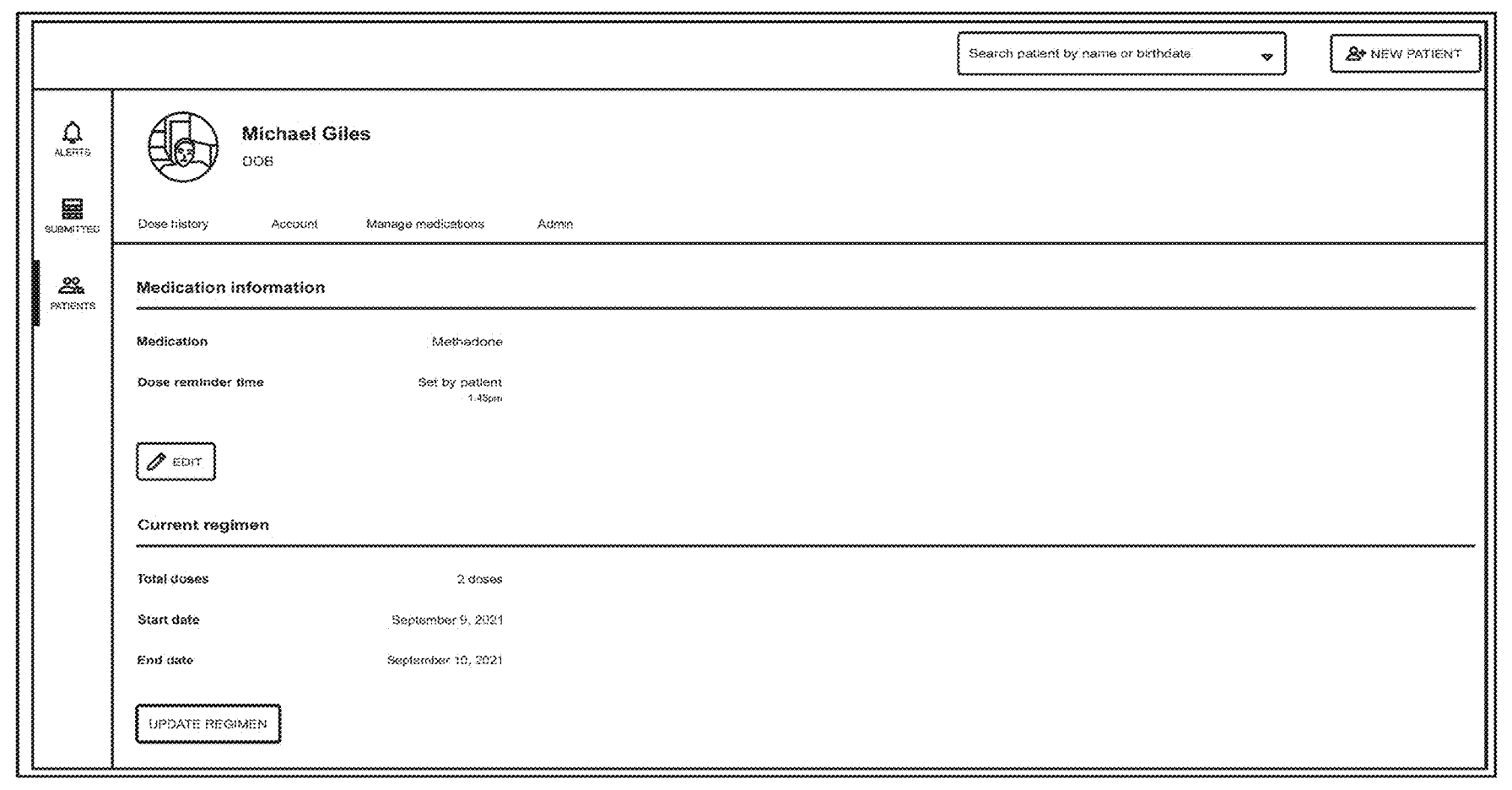

FIG. 6F shows an example of the patient page which may include a manage medications page. The manage medication page may include information about the medication and current dosage regime, although not limited thereto. The medication information may include the medication type and a dosage reminder time include who set the dosage reminder. The current dosage regime information may include the number of doses in the regime and the start and end date of the regime, although not limited thereto. The medication and/or the dosage regime information may be edited/updated.

Although the invention has been illustrated and described herein with reference to a preferred embodiment and a specific example thereof, it will be readily apparent to those of ordinary skill in the art that other embodiments and examples may perform similar functions and/or achieve user experiences. All such equivalent embodiments and examples are within the spirit and scope of the present invention, are contemplated thereby, and are intended to be covered by the disclosure.

While the present teachings have been described above in terms of specific embodiments, it is to be understood that they are not limited to those disclosed embodiments. Many modifications and other embodiments will come to mind to those skilled in the art to which this pertains, and which are intended to be and are covered by both this disclosure and the appended claims. For example, in some instances, one or more features disclosed in connection with one embodiment can be used alone or in combination with one or more features of one or more other embodiments. It is intended that the scope of the present teachings should be determined by proper interpretation and construction of any claims and their legal equivalents, as understood by those of skill in the art relying upon the disclosure in this specification and the attached drawings.

What is claimed is:

1. A system for monitoring drug delivery, comprising:
    a container having:
        a medicine disposed inside, the medicine associated with a patient;
        a machine-readable code on an outside of the container;
        wherein the machine-readable code must be broken to open the container;
        a second code in an interior of the container not accessible before the machine-readable code is broken;
    a user device having:
        a camera;
        software executing on a computer readable medium for:
            initiating recording of a video with the camera;
            prompting the patient to show the machine-readable code in the video;
            prompting the patient to show the second code in the video;
            prompting the patient to show the taking of the medicine in the video;
    a computer receiving the video, the computer having:
        a datastore with a plurality of profiles, one of the plurality of profiles being a patient profile associated with the patient;
        software executing on a computer readable medium for:

storing the video and associating the video with the patient profile;

verifying the association of the medicine and the patient using the machine-readable code;

verifying association of the machine-readable code and the patient using the second code;

identifying movement of the patient in the video using a machine learning algorithm and event interpretation;

generating a score indicative of the likelihood the medicine was taken by the patient by weighing factors such as the verification that the medicine is associated with the patient, and the identified movements of the patient.

2. The system of claim 1, wherein the software executing on a computer readable medium for identifying movement of the patient determines whether the patient took the medicine.

3. The system of claim 1, the computer having software executing on a computer readable medium for identifying the medicine and generating the score based on the identity of the medicine.

4. The system of claim 1, wherein the machine-readable code is encrypted.

5. The system of claim 4, further comprising:
the computer having software executing on a computer readable medium for decrypting the machine-readable code with the second code.

6. The system of claim 1, wherein the machine-readable code is at least one of a bar-code, a QR code, an NFC tag, and an infrared tag.

7. The system of claim 1, further comprising the user device having software executing on a computer readable medium for prompting the patient to perform an action.

8. The system of claim 7, wherein the action is a physical move.

9. The system of claim 7, the user device having a microphone for recording sound synchronized with the video, and wherein the action is saying a phrase.

10. The system of claim 1, wherein the datastore is an immutable ledger.

11. The system of claim 1, the user device having software executing on a computer readable medium for providing feedback when the camera records the first code, the feedback being at least one of a notification, a sound, a vibration, or a flash.

12. The system of claim 1, the computer further having software executing on a computer readable medium for sending a notification if the score exceeds a threshold.

13. The system of claim 12, wherein the notification prompts the patient to input a reason for why the score exceeds a threshold.

14. The system of claim 12, wherein the notification is sent to a provider device with the video.

15. The system of claim 1, the computer further having software executing on a computer readable medium for providing a reward to the user device if the score exceeds a threshold.

16. The system of claim 1, further comprising:
a provider device having:
software executing on a computer readable medium for:
receiving and displaying the score and the video;
receiving a user input adjusting the score; and
transmitting the user input to the datastore.

17. The system of claim 16, wherein at least one of the video, score, and the adjusted score is used to generate scores for future videos.

18. A system for monitoring drug delivery, comprising:
a container having:
a medicine disposed inside, the medicine associated with a patient;
a machine-readable code on an outside of the container;
wherein the machine-readable code must be broken to open the container;
a second code in an interior of the container not accessible before the machine-readable code is broken;
a user device having:
a camera;
software executing on a computer readable medium for:
initiating recording of a video with the camera;
prompting the patient to show the machine-readable code in the video;
prompting the patient to show the second code in the video;
prompting the patient to show the taking of the medicine in the video;
a computer receiving the video, the computer having:
a datastore with a plurality of profiles, one of the plurality of profiles being a patient profile associated with the patient;
software executing on a computer readable medium for:
storing the video and associating the video with the patient profile;
verifying the association of the medicine and the patient using the machine-readable code;
verifying association of the machine-readable code and the patient using the second code;
identifying movement of the patient in the video using a machine learning algorithm and event interpretation;
generating a score indicative of the likelihood the medicine was taken by the patient by weighing factors such as the verification that the medicine is associated with the patient, and the identified movements of the patient; and
a provider device having:
software executing on a computer readable medium for:
receiving and displaying the score and the video;
receiving a user input adjusting the score; and
transmitting the user input to the datastore.

* * * * *